US00RE38425E

(19) United States
(12) Reissued Patent
Dimmock et al.

(10) Patent Number: US RE38,425 E
(45) Date of Reissued Patent: Feb. 10, 2004

(54) SEMICARBAZONES HAVING CNS ACTIVITY AND PHARMACEUTICAL PREPARATIONS CONTAINING SAME

(75) Inventors: Jonathan Richard Dimmock, Saskatoon (CA); Ramanan Narayan Puthucode, Richland, WA (US)

(73) Assignee: University of Saskatchewan Technologies, Inc., Saskatoon (CA)

(21) Appl. No.: 09/556,910

(22) Filed: Apr. 20, 2000

Related U.S. Patent Documents

Reissue of:
(64) Patent No.: 5,741,818
Issued: Apr. 21, 1998
Appl. No.: 08/475,313
Filed: Jun. 7, 1995

(51) Int. Cl.[7] ..... A61K 31/375; C07C 281/14
(52) U.S. Cl. ..... 514/490; 564/36
(58) Field of Search ..... 514/590, 588, 514/582, 583; 564/36, 19, 20, 21

(56) References Cited

U.S. PATENT DOCUMENTS

| | | | | |
|---|---|---|---|---|
| 3,139,458 | A | 6/1964 | Paquette | 260/554 |
| 3,213,139 | A | 10/1965 | Chase et al. | 260/570 |
| 3,251,064 | A | 5/1966 | Schultz et al. | 260/294 |
| 3,255,241 | A | 6/1966 | Schultz et al. | 260/516 |
| 3,300,484 | A | 1/1967 | Pappo | 260/239.5 |
| 3,303,214 | A | 2/1967 | Anderson et al. | 260/554 |
| 3,304,323 | A | 2/1967 | Fonken et al. | 260/488 |
| 3,324,121 | A | 6/1967 | Sprague | 260/247.2 |
| 3,392,171 | A | 7/1968 | Fonken et al. | 260/247.7 |
| 3,558,654 | A | 1/1971 | Bamford et al. | 260/326.83 |
| 3,712,914 | A | 1/1973 | Tilles | 260/479 C |
| 4,015,011 | A | 3/1977 | Schromm et al. | 424/324 |
| 4,394,514 | A | 7/1983 | Kruse | 548/508 |
| 4,454,337 | A | 6/1984 | Kruse | 560/22 |
| 5,236,957 | A | 8/1993 | Dostert et al. | 514/620 |
| 5,266,585 | A | 11/1993 | Hubele et al. | 514/383 |
| 5,391,577 | A | 2/1995 | Dostert et al. | 514/620 |
| 5,502,079 | A | 3/1996 | Dostert et al. | 514/620 |
| 5,665,673 | A | 9/1997 | Anderson et al. | 504/130 |
| 5,998,470 | A | 12/1999 | Halbert et al. | 514/482 |

FOREIGN PATENT DOCUMENTS

| | | |
|---|---|---|
| BE | 612 755 | 7/1962 |
| BE | 622 079 | 3/1963 |
| BE | 639 727 | 5/1964 |
| BE | 667 022 | 11/1965 |
| EP | 0 065 485 B1 | 11/1982 |
| WO | WO 94/06758 A1 | 3/1994 |
| WO | WO 95/31448 A1 | 11/1995 |
| WO | WO 96/40628 | 12/1996 |
| WO | WO 97/16433 A1 | 5/1997 |

OTHER PUBLICATIONS

Facsimile letter dated Mar. 30, 2001, from Charles E. Phipps (Locke Liddell & Sapp LLP) to Howard R. Udell (Executive Vice President and General Counsel, Purdue Pharma L.P.) and Bob Sadler (University of Saskatchewan Technologies Inc.).

Facsimile letter dated Apr. 9, 2001, from Branko F. Peterman (President & CEO, University of Saskatchewan Technologies Inc.) to Charles E. Phipps (Locke Liddell & Sapp LLP).

Facsimile letter dated Apr. 20, 2001, from Branko F. Peterman (President & CEO, University of Saskatchewan Technologies Inc.) to Charles E. Phipps (Locke Liddell & Sapp LLP) enclosing a facsimile letter dated Apr. 19, 2001, from Norris M. Eades (Kirby, Eades, Gale, Baker) to Bin Yan (University of Sadkatchewan Technologies Inc.).

Facsimile letter dated May 3, 2001, from Charles E. Phipps (Locke Liddell & Sapp LLP) to Branko F. Peterman (President & CEO, University of Saskatchewan Technologies Inc.).

Facsimile letter dated Aug. 8, 2001, from Charles E. Phipps (Locke Liddell & Sapp LLP) to Bin Yan (University of Saskatchewan Technologies Inc.) enclosing "a copy of a Complaint".

Complaint, filed Sep. 24, 2001, *Puthucode v. Godici,* United States District Court for the Northern District of Texas, case No. 3:01CV1902–D.

Defendant's Motion to Dismiss (with prejudice), filed Nov. 21, 2001, *Puthucode v. Godici,* United States District Court for the Northern District of Texas, case No. 01–CV–1902–D.

Notice of Voluntary Dismissal, filed Nov. 30, 2001, *Puthucode v. Godici,* United States District Court for the Northern District of Texas, case No. 3–01CV1902–D.

Order, filed Nov. 30, 2001, *Puthucode v. Godici,* United States District Court for the Northern District of Texas, case No. 3:01–CV–1902–D.

Complaint, filed Jan. 2, 2002, *Puthucode v. The University of Saskatchewan Technologies, Inc.,* United States District Court for the District of Columbia, case No. 1:02CV00001.

Defendant UST's Motion to Dismiss for Failure to Join Necessary and Indispensable Parties, dated Feb. 19, 2002, *Puthucode v. The University of Saskatchewan Technologies, Inc.,* United States District Court for the District of Columbia, case No. 1:02CV00001.

(List continued on next page.)

*Primary Examiner*—Deborah C. Lambkin
(74) *Attorney, Agent, or Firm*—Sterne, Kessler, Goldstein & Fox P.L.L.C.

(57) ABSTRACT

A compound of general formula I below useful as an anticonvulsant for disorders of the central nervous system:

wherein: $R^1$, $R^2$, $R^3$ and $R^4$ may be the same or different and each represents a hydrogen or halogen atom, or a $C_{1-9}$ alkyl, $C_{3-9}$cycloalkyl, cyano, $C_{1-9}$alkoxy or $C_{6-10}$aryloxy group; $R^5$ represents a hydrogen atom or a $C_{1-9}$alkyl, $C_{3-9}$cycloalkyl or $C_{6-10}$aryl group; and X is oxygen or sulfur; or a pharmaceutically-acceptable salt thereof. The compound may be adimistered orally for treating convulsions in humans or animals.

38 Claims, 3 Drawing Sheets

OTHER PUBLICATIONS

Memorandum Opinion and Order, dated Mar. 28, 2002, *Puthucode v. The University of Saskatchewan Technologies, Inc.,* United States District Court for the District of Columbia, case No. 1:02CV00001.
Memorandum from J.R. Dimmock to R.N. Puthucode dated Dec. 29, 1992.
Memorandum from J.R. Dimmock to R.N. Puthucode dated Jun. 7, 1993.
Memorandum from J.R. Dimmock to R.N. Puthucode dated Nov. 16, 1993.
Memorandum from J.R. Dimmock to R.N. Puthucode dated Mar. 30, 1994.
Memorandum from J.R. Dimmock to R.N. Puthucode dated Jul. 26, 1994.
Memorandum from J.R. Dimmock to R.N. Puthucode dated Mar. 28, 1995.
J.R. Dimmock, Project Notes: Sep. 3, 1993; Sep. 8, 1993; Aug. 31, 1993; Mar. 24, 1994; Mar. 25, 1994; Mar. 19, 1994; Jan. 6, 1995 and an undated project note.
J.R. Dimmock, Notes for Weekly Meetings with Puthucode, from Feb. 12, 1993 to Mar. 8, 1996.
Ramanan, P.N., N.B. #3, Feb. 7, 1994 to May 4, 1995.
Ramanan, P.N., Laboratory Notebook, May 8, 1995 to Mar. 21, 1996.
Memorandum dated Apr. 19, 1995, from J.R. Dimmock to Mr. B. Sadler (University of Saskatchewan Technologies Inc.), copied to RNP [R.N. Puthucode].
Puthucode, N.R., "Synthesis and Anticonvulsant Evaluation of Some Aryl Semicarbazones," Report No. 2 (Sep. 1995).
Puthucode, R.N., "Design and Synthesis of Some Aryloxyaryl Semicarbazones and Related Compounds as Novel Anticonvulsants," Ph.D. Thesis, The University of Saskatchewan, Canada, 202 pp., UMI Dissertation Services (Spring 1996).
Memorandum dated Oct. 4, 1995 from J.R. Dimmock to "To Whom It May Concern".
Memorandum dated Jun. 9, 1997, from J.R. Dimmock to "To Whom It May Concern".
Dimmock, J.R. et al., "(Aryloxy)aryl Semicarbazones and Related Compounds: A Novel Class of Anticonvulsant Agents Possessing High Activity in the Maximal Electroshock Screen," *Journal of Medicinal Chemistry 39*:3984–3997, American Chemical Society (1996).
Dimmock, J.R. et al., "Structural modifications of the primary amino group of anticonvulsant aryl semicarbazones," *Pharmazie 51*:83–88, Govi–Verlag Pharmazeutischer Verlag GmbH Eschborn (1996).
Gorbacheva, I.N. et al., "Synthesis of Substituted Diphenyl Ethers," *Journal of General Chemistry of the USSR 25*:2259–2263, Consultants Bureau, Inc. (1955).
Trust, R.I. et al., "(Aryloxy) [p– (aryloxy)phenyl]– and (Aryloxy) [p– (arylthio)phenyl]acetic Acids and Esters as Hypolipidemic Agents," *Journal of Medicinal Chemistry 22*:1068–1074, American Chemical Society (1979).
Dimmock, J.R. et al., "Evaluation of acrylophenones and related bis–Mannich bases against murine P388 leukemia," *European Journal of Medicinal Chemistry 22*:545–551, Elsevier (1987).
American Chemical Society, CAS file CAOLD, see Registry No. 115229–17–9, 1988.
American Chemical Society, CAS file CAOLD, see Registry No. 114399–26–7, 1988.
American Chemical Society, CAS file CAOLD, see Registry No. 107921–04–0, 1987.
American Chemical Society, CAS file CAOLD, see Registry No. 101091–62–7, 1987.
American Chemical Society, CAS file CAOLD, see Registry No. 95135–19–6, 1985.
American Chemical Society, CAS file CAOLD, see Registry No. 94960–09–5, 1985.
American Chemical Society, CAS file CAOLD, see Registry No. 93899–42–4, 1985.
American Chemical Society, CAS file CAOLD, see Registry No. 93651–16–2, 1985.
American Chemical Society, CAS file CAOLD, see Registry No. 92968–95–1, 1985.
American Chemical Society, CAS file CAOLD, see Registry No. 1158–22–1, 1968.
American Chemical Society, CAS file CAPLUS, see Registry No. 36934–63–1 and 36934–64–2, 1973.
American Chemical Society, CAS file CAPLUS, see Registry No. 174521–23–4, 1996.
American Chemical Society, CAS file CAPLUS, see Registry No. 190657–77–3, 1998.
American Chemical Society, CAS file CAPLUS, see Registry No. 144141–11–7, 1993.
American Chemical Society, CAS file CAPLUS, see Registry No. 54291–81–5, 1975.
American Chemical Society, CAS file CAPLUS, see Registry No. 22263–45–2, 1970.
Badische Anilin & Soda–Fabrik A.–G., "Terephthaldialdehyde," *Chemical Abstracts 65,* abstract 5405b, American Chemical Society (1966). See 5412e.
Baltzly, R. et al., "2,4–Diamino–5–[4'–fluoro–3'–halogenophenyl]pyrimidines," *J. Organic Chem. 26*:2353–2355, American Chemical Society (1961).
Bayoumy, B. E.–S. and L. Skulski, "Synthesis of Some New Diaryl Sulphides and Diaryl Sulphones Containing 1,2, 3–Thiadiazole Moiety," *Bull. Pol. Acad. Sci. Chem. 39*:455–458, Warsaw (1991).
Beilstein Informationgesellschaft GmbH, see Belstein Registry No. 2541223, 1940.
Beilstein Informationgesellschaft GmbH, see Belstein Registry No. 1890700, 1940.
Beilstein Informationgesellschaft GmbH, see Belstein Registry No. 3400167, 1940.
Beilstein Informationgesellschaft GmbH, see Belstein Registry No. 3400193, 1940.
Beilstein Informationgesellschaft GmbH, See Belstein Registry No. 3410343, 1940.
Beilstein Informationgesellschaft GmbH, see Belstein Registry No. 3419487, 1940.
Beilstein Informationgesellschaft GmbH, see Belstein Registry No. 3421220, 1940.
Beilstein Informationgesellschaft GmbH, see Belstein Registry No. 3436628, 1940.
Beilstein Informationgesellschaft GmbH, see Belstein Registry No. 3396690, 1939.
Beilstein Informationgesellschaft GmbH, see Belstein Registry No. 3389800, 1939.
Beilstein Informationgesellschaft GmbH, see Belstein Registry No. 3417848, 1940.
Beilstein Informationgesellschaft GmbH, see Belstein Registry No. 3422330, 1940.
Beilstein Informationgesellschaft GmbH, see Belstein Registry No. 3449771, 1940.

Beilstein Informationgesellschaft GmbH, see Belstein Registry No. 3382967, 1940.
Beilstein Informationgesellschaft GmbH, see Belstein Registry No. 3347507, 1940.
Beilstein Informationgesellschaft GmbH, see Belstein Registry No. 3468481, 1941.
Beilstein Informationgesellschaft GmbH, see Belstein Registry No. 3468486, 1941.
Beilstein Informationgesellschaft GmbH, see Belstein Registry No. 3508814, 1941.
Beilstein Informationgesellschaft GmbH, see Belstein Registry No. 5349918, 1945.
Beilstein Informationgesellschaft GmbH, see Belstein Registry No. 3532377, 1941.
Beilstein Informationgesellschaft GmbH, see Belstein Registry No. 3178769, 1940.
Demetresco, C. et al., "p–Alkoxyphenyl p–substituted–phenyl sulfone series. III. Derivatives with potential pharmacodynamic action," *Chim. Ther. 3*:343–347, Societe Francaise de Chimie Therapeutique; Editions Scientifiques et Medicale Elsevier (1968). [In French].
Demetresco, C. et al., "p–Alkoxyphenyl p–substituted–phenyl sulfone series. III. Derivatives with potential pharmacodynamic action," *Chemical Abstracts 70,* abstract 106164s, American Chemical Society (1969).
Dimmock, J.R. et al., "Evaulation of the thiosemicarbazones of some aryl alkyl ketones and related compounds for anticonvulsant activities," *Eur. J. Med. Chem. 26*:529–534, Elsevier (1991).
Dimmock, J.R. et al., "Evaluation of some Mannich bases of 1–aryl–1–ethanones and related ketones for anticonvulsant activities," *Pharmazie 46*:538–539, Verlag Gesundheit GmbH (1991).
Dimmock, J.R. et al., "Anticonvulsant Activities of Some Arylsemicarbazones Displaying Potent Oral Activity in the Maximal Electroshock Screen in Rats Accompanied by High Protection Indices," *J. Med. Chem 36*:2243–2252, American Chemical Society (1993).
Dimmock, J.R. et al., "Some aryl semicarbazones possessing anticonvulsant activities," *Eur. J. Med. Chem. 30*:287–301, Elsevier (1995).
English language translation of Horii, Z. and T. Kinouchi, "On Hydrazones, which are Derived from p–Thiocyanatophenylhydrazine (Part IV)," *Yakugaku Zasshi* (*J. Pharm. Soc. Japan*) *57*:123–124, Nippon Yakugakkai (1937).
English language translation of Ito, G., "Synthesis of Guanidine Compounds of Diphenyl Ethers. I.," *Pharm. Bull.* (*Tokyo*) *5*:397–400, Pharmaceutical Society of Japan (1957).
English language translation of Ito, G., "Synthesis of Guanidine Compounds of Diphenyl Ether II. A New Synthesis of Diphenyl Ether Aldehyde According to Sommelet and Experiments with Methylguanidine Derivatives (1).," *Pharm. Bull* (*Tokyo*) *5*:401–405, Pharmaceutical Society of Japan (1957).
English language translation of Julia, M.M. and M. Baillarge, "Plant Growth Factors. IV. Some Substituted p–Phenoxy–phenylacetic Acids," *Bull. Soc. Chim. Fr., Fifth Series. 20*:644–647, Masson et Cie (1953).
English language translation of Kimoto, S. et al., "Syntheses of Allied Compounds of Chloramphenicol I.," *Yakugaku Zasshi* (*J. Pharm. Soc. Japan*) *72*:496–497, Pharmaceutical Society of Japan (1952).
English language translation of Kimoto. S. and K. Asaki, "Studies on the Friedel–Crafts Reaction in Diphenyl Ether Derivatives. Part II.," *Yakugaku Zasshi* (*J. Pharm. Soc. Japan*) *72*:300–303, Pharmaceutical Society of Japan (1952).
English language translation of Kimoto, S. et al., "Studies on the Friedel–Crafts Reaction of Diphenyl Ether Derivatives. III.," *Yakugaku Zasshi* (*J. Pharm. Soc. Japan*) *73*:243–244, Pharmaceutical Society of Japan (1953).
English language translation of Kimoto, S. et al., "Studies on The Friedel–Crafts Reaction of Diphenyl Ether Derivatives. VI. Reaction of Monochlorodiphenyl Ether and Acetyl Chloride," *Yakugaku Zasshi* (*J. Pharm. Soc. Japan*) *74*:358–360, Pharmaceutical Society of Japan (1954).
English language translation of Tomita, M. et al., "Synthesis of Aldehyde Derivatives Containing a Diphenyl Ether Unit," *Yakugaku Zasshi* (*J. Pharm. Soc. Japan*) *75*:1021–1023, Pharmaceutical Society of Japan (1955).
Faltis,F. et al., "Biscoclaurine Alkaloids. Constitution of Chondodendrine and Trilobine," *Chem. Ber. 74*:79–97, Verlag Chemie GmbH (1941). [In German].
Faltis,F. et al., "Bisoclaurine Alkaloids. Constitution of Chondodendrine and Trilobine," *Chemical Abstracts 35,* abstract 5121f, American Chemical Society (1941).
Fujikawa, F. et al., "Syntheses of Depsidones. I.," *Yakugaku Zasshi* (*J. Pharm. Soc. Japan*) *63*:1172–1174, Pharmaceutical Society of Japan (1963). [In Japanese].
Fujikawa, F. et al., "Syntheses of Depsidones. I.," *Chemical Abstracts 60,* abstract 10685d, American Chemical Society (1964).
Harington, C.R., "Chemistry of Thyroxine. II. Constitution and Synthesis of Desiodo–Thyroxine," *Biochem. J. 20*:300–313, London Portland Press (1926).
Harington, C.R. and R.V. Pitt Rivers, "A New Synthesis of Thyronine," *J. Chem. Soc.* 1101–1103, The Chemical Society (1940).
Horii, Z. and T. Kinouchi, "On Hydrazones, which are Derived from p–Thiocyanatophenylhydrazine (Part IV)," *Yakugaku Zasshi* (*J. Pharm. Soc. Japan*) *57*:123–124, Nippon Yakugakkai (1937). [In German].
Ingersoll, A.W. et al., "Extensions of the Leuckart Synthesis of Amines," *J. Am. Chem. Soc. 58*:1808–1811, Mack Printing Co. (1936).
Ito, G., "Synthesis of Guanidine Compounds of Diphenyl Ether II. A New Synthesis of Diphenyl Ether Aldehyde According to Sommelet and Experiments with Methylguanidine Derivatives (1).," *Pharm. Bull.* (*Tokyo*) *5*:401–403, Pharmaceutical Society of Japan (1957). [In German].
Ito, G., "Synthesis of Guanidine Compounds of Diphenyl Ethers. I.," *Pharm. Bull.* (*Tokyo*) *5*:397–400, Pharmaceutical Society of Japan (1957). [In German].
Julia, M.M. and M. Baillarge, "Plant Growth Factors. IV. Some Substituted p–Phenoxy–phenylacetic Acids," *Bull. Soc. Chim. Fr., Fifth Series, 20*:644–647, Massson et cie (1953). [In French].
Kimoto, S. et al., "Syntheses of Allied Compounds of Chloramphenicol I.," *Yakugaku Zasshi* (*J. Pharm. Soc. Japan*) *72*:496–497, Pharmaceutical Society of Japan (1952). [In Japanese].
Kimoto. S. and K. Asaki, "Studies on the Friedel–Crafts Reaction in Diphenyl Ether Derivatives. Part II.," *Yakugaku Zasshi* (*J. Pharm. Soc. Japan*) *72*:300–303, Pharmaceutical Society of Japan (1952). [In Japanese].

Kimoto, S. et al., "Studies on the Friedel–Crafts Reaction of Diphenyl Ether Derivatives, III.," *Yakugaku Zasshi* (*J. Pharm. Soc. Japan*) *73*:243–244, Pharmaceutical Society of Japan (1953). [In Japanese].

Kimoto, S. et al., "Studies on the Friedel–Crafts Reaction of Diphenyl Ether Derivatives. VI. Reaction of Monochlorodiphenyl Ether and Acetyl Chloride," *Yakugaku Zasshi* (*J. Pharm. Soc. Japan*) *74*:358–360, Pharmaceutical Society of Japan (1954). [In Japanese].

Krall, R.L. et al., "Antiepileptic Drug Development: II. Anticonvulsant Drug Screening," *Epilepsia 19*:409–428, Raven Press (1978).

Nerurkar, J.J. et al., β–Arylglutaconic acids. IV. Synthesis of crotono– and valerolactones of β–arylglutaconic and glutaric acids. *J. Org. Chem. 25*:1491–1495, American Chemical Society (1960).

Ochiai, E. and Y. Tamai, "Friedel–Crafts Reaction of Diphenyl Ethers with Succinic Acid Chloride," *Itsuu Kenkyusho Nempo, No. 12*:39–41, Research Foundation Itsuu Laboratory (1962). [In German].

Ochiai, E. and Y. Tamai, "Friedel–Crafts Reaction of Diphenyl Ethers with Succinic Acid Chloride," *Chemical Abstracts 59*, abstract 7414b, American Chemical Society (1963).

Racine, R.J., "Modification of Seizure Activity by Electrical Stimulation: II. Motor Seizure," *Electroenceph. Clin. Neurophysiol. 32*:281–294, Elsevier Publishing Co. (1972).

Rubinchik, M.A. and O.N. Tolkachev, "Study of the antiprotozoal activity of compounds of a group of diphenyl ethers and some nitrostyrenes," *Med. Parazitol. Parazit. Bolezni 45*:531–536, Izd–Vo "Meditsina" (1976). [In Russian].

Rubinichik, M.A. and O.N. Tolkachev, "Study of the antiprotozoal activity of compounds of a group of diphenyl ethers and some nitrostyrenes," *Chemical Abstracts 86,* abstract 115615x, American Chemical Society (1977).

Samaritoni, J.G. et al., "Methylene Group Modifications of the N–(Isothiazol–5–yl)phenylacetamides. Synthesis and Insecticidal Activity," *J. Agric. Food Chem. 47*:3381–3388, American Chemical Society (Aug. 1999).

Skeen, G. et al., "Development of Kindled Seizures Following Electrical Stimulation via the Cornea," *Soc. Neurosci. Abstracts 16*:307, Abstract No. 138.1, Society for Neuroscience (1990).

Tomimatsu, T. and Y. Kano, "Alkaloids of *Thalictrum thunbergii.* XIII. Structure of thalicberine and O–methylthalicberine. 5.," *Yakugaku Zasshi* (*J. Pharm. Soc. Japan*) *83*:153–158, Pharmaceutical Society of Japan (1963). [In Japanese].

Tomimatsu, T. and Y. Kano, "Alkaloids of *Thalictrum thunbergii.* XIII. Structure of thalicberine and O–methylthalicberine. 5.," *Chemical Abstracts 59*, abstract 3971b, American Chemical Society (1963).

Tomita, M. et al., "Synthesis of Aldehyde Derivatives Containing a Diphenyl Ether Unit," *Yakugaku Zasshi* (*J. Pharm. Soc. Japan*) *75*:1021–1023, Pharmaceutical Society of Japan (1955). [In Japanese].

Ungnade, H.E. and E.F. Orwoll, "The Gattermann Reaction in the Mono–methoxydiphenyl Ethers," *J. Am. Chem. Soc. 65*:1736–1738, Mack Printing Co. (1943).

Vichkanova, S.A. et al., "Structure and antituberculous activity of some diphenyl ethers," *Farmakol. Toksikol.* (*Moscow*) *37*:711–715, Gosudarstrennoe izd–vomeditsinskoi literatur (1974). [In Russian].

Vichkanova, S.A. et al., "Structure and antituberculous activity of some diphenyl ethers," *Chemical Abstracts 82*, abstract 106878a, American Chemical Society (1975).

Volynskaya, E.M. et al., "Monophosphonium salts and monophosphoranes based on 4,4'–diacetylbiphenyl and its derivatives," *Zh. Obshch. Khim. 42*:986–992, Maik Nauka (1972). [In Russian].

Volynskaya, E.M. et al., "Monophosphonium salts and monophosphoranes based on 4,4'–diacetylbiphenyl and its derivatives," *Chemical Abstracts 77*, abstract 101775b, American Chemical Society (1972).

Walker, J., "Experiments on the Synthesis of Potential Cortical Hormone Substitutes. Hydroxycarbonyl Derivatives of Diphenyl Ether and Related Compounds," *J. Chem. Soc.* 347–353, The Chemical Society (1942).

Yeager, G.W. and D.N. Schissel, "A Convenient Method for the Preparation of 4–Aryloxyphenols," *Synthesis* (*1*):63–68, Georg Thieme Verlag Stuttgart, Thieme Medical Publishers, Inc. (1991).

International Search Report of International Application No. PCT/CA96/00380, filed Jun. 7, 1996.

Abstract of Hungarian Patent No. 189136, published Apr. 28, 1984.

Abstract of Hungarian Patent No. 214006, published Jun. 28, 1995.

Novelty Search Report of Hungarian Patent Application No. P98 02637, completed Aug. 23, 2000.

Chemical Abstract 50 4836 (1956).*

* cited by examiner

2

4

3

5

SEMICARBAZONES HAVING CNS ACTIVITY AND PHARMACEUTICAL PREPARATIONS CONTAINING SAME

Matter enclosed in heavy brackets [ ] appears in the original patent but forms no part of this reissue specification; matter printed in italics indicates the additions made by reissue.

BACKGROUND OF THE INVENTION

I. Field of the Invention

This invention relates to semicarbazone compounds having central nervous system (CNS) activity and to pharmaceutical preparations containing such compounds. More particularly, the invention relates to semicarbazones having anticonvulsant properties and to the use of such semicarbazones for the treatment or prevention of convulsions and seizures in humans and animals.

II. Description of the Prior Art

There has been a great deal of interest for many years in the identification of drugs that exhibit central nervous system activity in humans and animals and that are, in particular, anticonvulsants used for the treatment or prevention of epileptic seizures and other central nervous system disorders.

A previous study carried out by one of the inventors of the present invention (Dimmock et al., J. Med. Chem., 1993, 36, pp. 2243–2252) revealed that a number of aryl semicarbazones of the general formula A

[A]

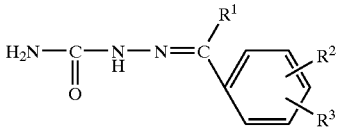

possess anticonvulsant activity in the maximal electroshock (MES) screen and the subcutaneous pentylenetetrazole (scPTZ) screen when administered by the intraperitoneal route to mice. These screens are test systems developed to detect compounds which will afford protection to generalized tonic-clonic seizures and generalized absence convulsions, respectively. The MES screen and the scPTZ screen have been discussed by Krall, et al. in "Antiepileptic drug development:II. Anticonvulsant drug screening", Epilepsia, 1978, 19, pp. 409–428; the disclosure of which is incorporated herein by reference.

Nevertheless, the compounds of formula A displayed neurotoxicity when administered by this route and the protection indices (PI, namely the ratio $TD_{50}/ED_{50}$) of ten representative compounds were low.

There is accordingly a need for compounds showing much improved anticonvulsive effects with reduced toxicity.

SUMMARY OF THE INVENTION

An object of the invention is to provide compounds having central nervous system activity.

Another object of the invention is to provide pharmaceutical compositions that have good anticonvulsive activity and acceptable neurotoxicity.

Yet another object of the invention is to provide methods of treating convulsions in humans and animal patients without producing unacceptable side effects.

According to one aspect of the invention, there is provided a compound of the general formula I

[I]

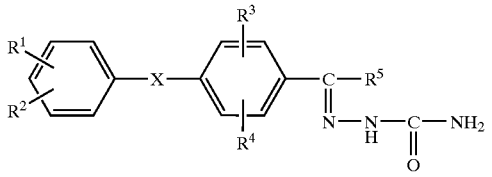

wherein: $R^1$, $R^2$, $R^3$ and $R^4$ may be the same or different and each represents a hydrogen or halogen atom, or a $C_{1-9}$alkyl, $C_{5-9}$cycloaliphatic, cyano, $C_{1-9}$alkoxy or $C_{6-10}$aryloxy group; $R^5$ represents a hydrogen atom or a $C_{1-9}$alkyl, $C_{3-9}$cycloalkyl or $C_{6-10}$aryl group; and X is oxygen or sulfur. In the compounds of the invention, the alkyl substituents, when present, may be straight-chained or branched.

It should be noted, however, that the compound of Formula I above in which $R^1$, $R^2$, $R^3$, $R^4$ and $R^5$ are all hydrogen is known from Tomita et. al., "Synthesis of Aldehyde Derivatives Containing a Diphenyl Ether Nucleus", J. Pharm. Soc. Japan, 1955, 75, 1021–1023, but this reference does not disclose the anticonvulsive property of the compound.

According to another aspect of the invention, there is provided a composition comprising a compound of general formula I and a pharmaceutically acceptable diluent, excipient or carrier.

According to yet another aspect of the invention, there is provided a method of treating diseases of the central nervous system of a human or animal patient, which comprises administering to said patient an effective amount of a compound of general formula I.

The compounds of the invention may be administered orally and may exhibit very high potencies against CNS convulsions, e.g. they may possess $ED_{50}$ figures (for the maximal electroshock screen in rats) in the 1–5 mg/kg range (more usually the 2–3 mg/kg range) while exhibiting an absence of neurotoxicity at the maximum dose utilized (e.g. 500 mg/kg), thus leading to extremely favourable protection index (PI) values.

The compounds of the invention appear to act by one or more mechanisms which are different from those of conventional anticonvulsant drugs. Moreover, the compounds of the invention may be free from some of the disadvantages of conventional anticonvulsant drugs since proconvulsant properties and effects on the activities of certain hepatic enzymes are absent in at least some of the compounds of the invention.

DETAILED DESCRIPTION OF TEE PREFERRED EMBODIMENTS METHODS OF SYNTHESIS

The compounds of the present invention and compounds having related structures can be synthesized by various chemical routes, e.g. by a modification of a method disclosed by Yeager et al. ("A Convenient Method for the Preparation of 4-Aryloxyphenols", Synthesis, 1991, pp. 63–68; the disclosure of which is incorporated herein by reference). Yeager et al. describes a process for producing aryloxybenzaldehydes or aryloxyaryl ketones. These intermediates may then be reacted with semicarbazides. This route is illustrated by the reaction scheme below:

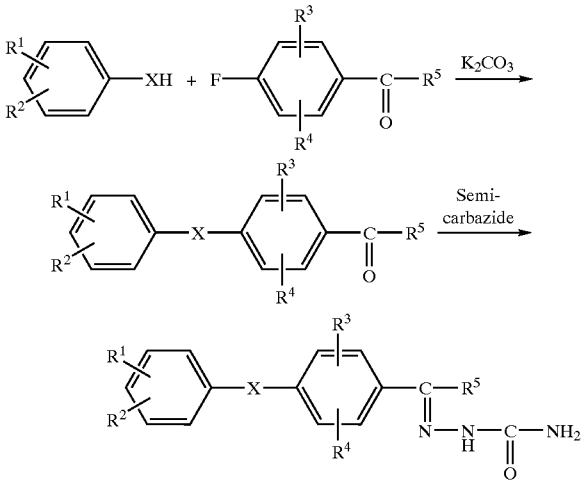

The reaction scheme shown above requires the formation of intermediate aryloxy- or arylthio-benzaldehydes or ketones by reacting appropriate phenols or thiophenols with fluorobenzaldehyde or fluoroaryl ketones in a suitable solvent (e.g. dimethylacetamide) in the presence of anhydrous potassium carbonate at temperatures in the range of 100° to 200° C. under atmospheric pressure of a non-oxidizing gas nitrogen) with reflux for a period of about 5–10 hours. After cooling and water addition, the intermediate compound may be extracted with an organic solvent (e.g. chloroform) and dried. The intermediate aryloxy(thio)benzaldehydes aryloxy (thio)aryl ketones are then converted into the desired semicarbazones by reaction with semicarbazide in an aqueous ethanolic solution for a period of one to several hours at ambient temperature, and the resulting precipitate of the final product is then collected and recrystallized. The starting materials, which are generally reacted in approximately stoichiometrical amounts, are themselves commercially available products and can, in particular, be obtained from the Aldrich Chemical Company, Milwaukee, USA.

Structures

Figure 1:
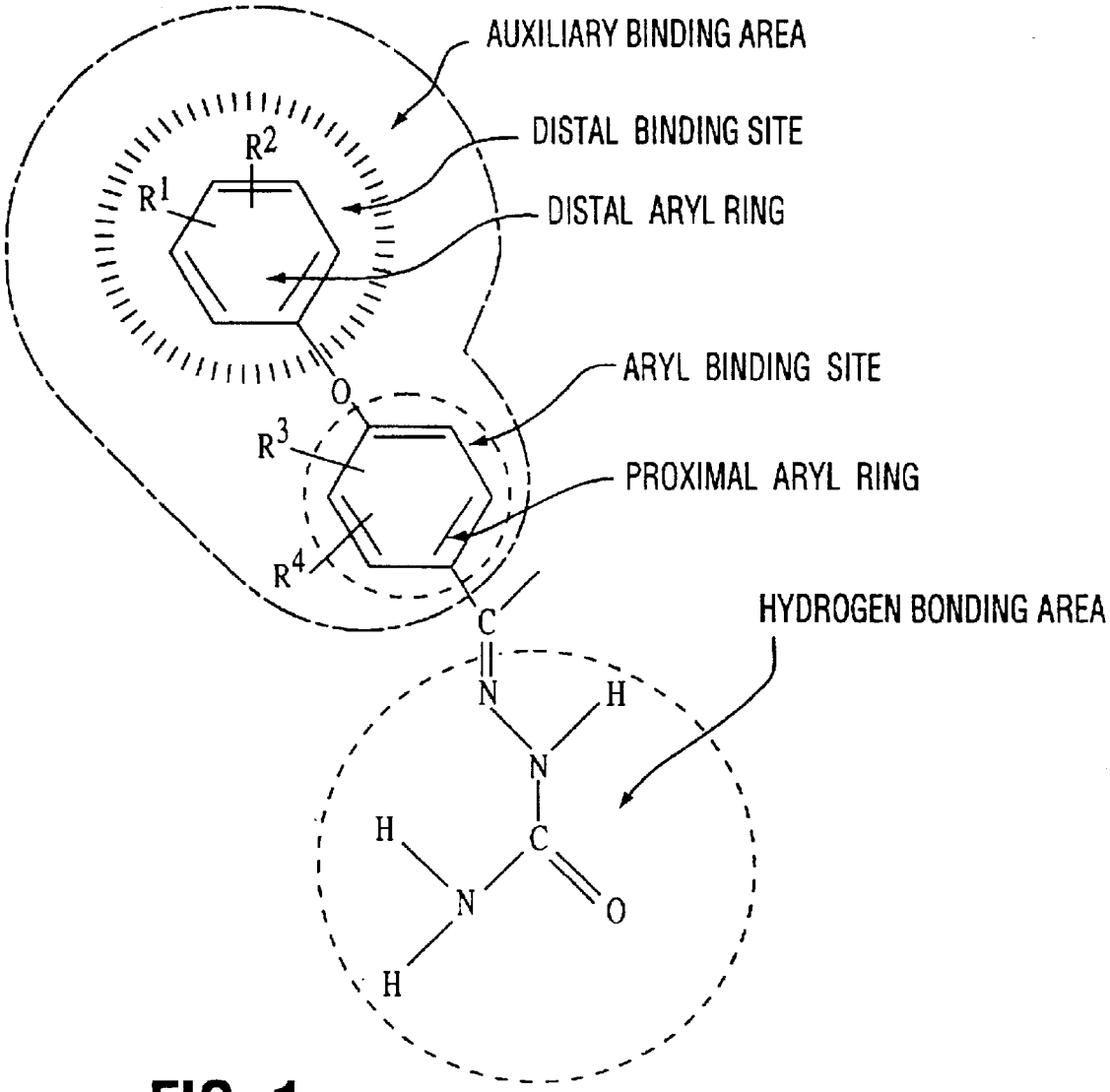
FIG. 1 is a simplified representation of the postulated receptor site showing different binding regions for the compounds according to the present invention.

Without wishing the invention to be limited to a particular theory, it is believed that the compounds of the present invention exert their anticonvulsive activity by aligning their molecules at a postulated receptor site in the human or animal brain, and it is theorized that such interactions take place at three areas of the receptor, namely an aryl binding site, a hydrogen bonding area and a distal binding site as illustrated in FIG. 1.

These sites are believed to react with the proximal aryl ring (the ring next to the semicarbazono group), the semicarbazono ($H_2NCONHN$=) group itself and the distal aryl ring of the compounds, respectively. The presence of the distal aryl ring and certain substituent groups on the distal and, to a lesser extent, the proximal aryl ring in the compounds of the invention appear to strengthen the attachment of the molecule at the receptor and thus increase the potency of the compounds.

A systematic synthesis and evaluation of compounds of Formula I and compounds with closely related structures has revealed the following general principles (i) The substitution of the methine hydrogen attached to the carbimino carbon atom by larger groups does not significantly affect the anticonvulsive activity of the compounds; (ii) positioning of the arlyoxy or arylthio group in the ortho or meta positions of the proximal ring leads to a lowering or abolition of anticonvulsive activity; (iii) the substitution of the ether oxygen by sulfur or sulfonyloxy groups leads to compounds with similar anticonvulsive activities, while other spacers lower the anticonvulsive potencies; (iv) a decrease in size of the substituents on the distal aryl ring, increases anticonvulsive activity; and (v) the anticonvulsive activity is high when at least one of the substitutents on the distal alkyl group is in the para position.

Hence, compounds of the present invention which are particularly preferred are those in which $R^1$ and $R^2$ are hydrogen or halogen (most preferably fluorine), $R^3$, $R^4$ are each hydrogen and $R^5$ is hydrogen or $C_{1-3}$ alkyl, and X is O or S (and most preferably O).

Particularly preferred compounds according to the present invention are 4-(4'-fluorophenoxy)benzaldehyde semicarbazone and 4-(thiophenoxy)benzaldehyde semicarbazone. These compounds exhibit high activity in the MES screen, low toxicity and afford protection in the corneal kindled rat screen without negative features, such as proconvulsant properties. Incidentally, the kindled rat screen is described by R. J. Racine in "Modification of Seizure Activity by Electrical Stimulation. II. Motor Seizure", Electroencephalogr.Clin.Neurophysiol., 1972, 32, 281–294, and by G. Skeen et al. In "Development of Kindled Seizures Following Electrical Stimulation via the Cornea", Soc.Neurosci., 1990, 16(1), 307; the disclosures of which are incorporated herein by reference.

Physiological Activity

The compounds of the present invention may in some cases have quite high neurotoxicity when injected intraperitoneally in mice. For example, neurotoxicity was found to be present in approximately 65% of the compounds tested and quantitation of the bioactivities of the compounds of the invention has revealed PI's in the range of 2–14 in the MES screen and 1–3 in the scPTZ screen. However, it has been found that such neurotoxicity disappears or is reduced to an acceptable level when the compounds are administered orally to rats. Moreover, while the compounds exhibit high activity in both the MES screen and the scPTZ screen when administered intra-peritoneally, the activity in the MES screen remains high when the compounds are administered orally, but the activity in the scPTZ screen may decline. For example, for the compound 4-(4'-fluorophenoxy) benzaldehyde semicarbazone, oral dosing of rats produced an $ED_{50}$ figure in the rat oral screen of 1.59 mg/kg and a PI of greater than 315. However, the compound did not afford protection in the scPTZ screen at a dose of 125 mg/kg and only 10% of the rats were protected at a dose of 250 mg/kg. An absence of neurotoxicity at the maximum dose utilized (500 mg/kg) led to exceptionally high protection indices.

Administration

The compounds of the invention may be administered orally to humans, preferably at dosages of 50–75 mg/kg, generally in the form of compositions with inert pharmaceutically-acceptable compounds, for example diluents (e.g. calcium phosphate dihydrate, calcium sulfate dihydrate, cellulose, dextrose, lactose, mannitol, starch, sorbitol, sucrose and sucrose-based materials), binders and adhesives (e.g. acacia, cellulose derivatives, gelatin, glucose, polyvinylpyrrolidone (PVP), alginates, sorbitol, pregelatinized starch or starch paste and tragacanth), disintegrants (e.g. alginates, cellulose and cellulose derivatives, clays, cross-linked PVP, starch and starch derivatives), lubricants (e.g. polyethylene glycols, stearic acids, salts and derivatives, surfactants, talc and waxes), glidants (cornstarch, silica derivatives and talc), and colors, flavors and sweeteners (e.g. FD&C and D&C dyes and lakes, flavor oils and spray-dried flavors, artificial sweeteners and natural sweeteners).

The compositions may be prepared in any one of the conventional forms for oral administration, e.g. powders, capsules, tablets, caplets, lozenges, solutions, syrups, etc.

The invention is described in more detail in the following Examples, which are nevertheless not intended to limit the scope of the invention.

EXAMPLE 1

Figure 2:
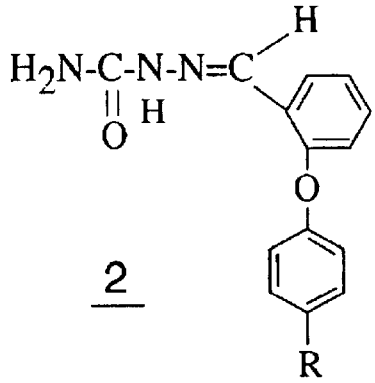
FIG. 2 shows basic skeletal structures to indicate the compounds listed in Tables 1 to 3.
Figure 2:
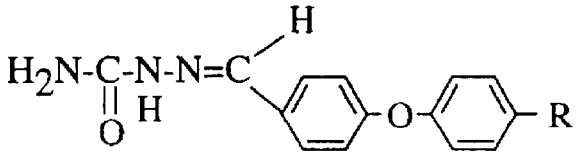
Figure 2:
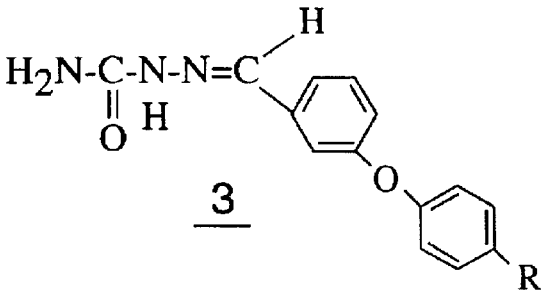
Figure 2:
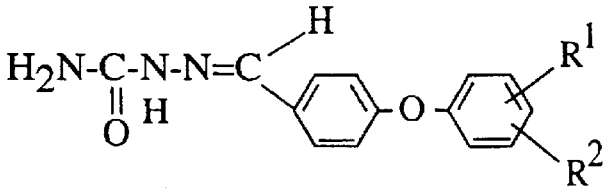

The compounds 2a to 5v shown in Table 1 below were synthesized by the method previously mentioned. The structures of the listed compounds correspond to those shown in FIG. 2 identified by the same first number (2, 3, 4 or 5), with only the substituents being identified in Table 1.

TABLE 1

Aryl Substituents, Physical Data and Anticonvulsant Evaluation after Intraperitoneal Injection into Mice and Oral Administration to Rats of the Compounds in Series 2–5

| | | | | intraperitoneal injection in mice[a] | | | | | | | oral administration to rats[b] | | | | |
|---|---|---|---|---|---|---|---|---|---|---|---|---|---|---|---|
| | aryl | | yield | MES screen | | acPTZ screen | | toxicity screen | | dose | MES screen | | | | |
| compound | substituents | m.p.(° C.) | % | 0.5 h | 4 h | 0.5 h | 4 h | 0.5 h | 4 h | (mg/kg) | 0.25 h | 0.5 h | 1 h | 2 h | 4 h |
| 2a | H | 198–199 | 40 | — | — | — | — | — | — | 50 | — | — | 2 | 1 | 1 |
| 2b | 4-F | 210–212 | 48 | — | — | — | — | — | — | 30 | 0 | 0 | 1 | 2 | 4 |
| 3 | H | 224–225 | 70 | — | 300 | — | — | — | — | 50 | — | — | — | — | — |
| 4a | H | 224–225 | 60 | 100 | 300 | — | — | — | — | 50 | — | 3 | 4 | 4 | 4 |
| 4b | 4-F | 233–234 | 65 | 30 | 100 | — | — | — | — | 50 | 2 | 4 | 4 | 4 | 4 |
| 4c | 4-Cl | 225–226 | 40 | 30 | 30 | 30 | — | 300 | 30 | 50 | 4 | 4 | 4 | 4 | 4 |
| 4d | 4-Br | 225–226 | 60 | 30 | 30 | — | — | 300 | 30 | 50 | 1 | 4 | 4 | 4 | 4 |
| 4e | 4-I | 221–222 | 71 | 30 | 30 | 100 | 300 | 300 | 100 | 50 | 3 | 4 | 4 | 4 | 4 |
| 4f | 4-$CH_3$ | 219–221 | 50 | 30 | 100 | — | — | — | — | 50 | 3 | 4 | 4 | 4 | 4 |
| 4g | 4-$C_6H_5$ | 280 | 72 | — | 300 | — | 300 | — | 300 | 12.5 | — | — | — | 3 | 1 |
| 4h | 4-$OCH_3$ | 218–220 | 60 | 100 | 100 | — | — | — | 300 | 50 | — | 4 | 4 | 4 | 4 |
| 4i | 4-$OC_6H_5$ | 209–210 | 55 | — | 300 | — | — | — | — | 50 | — | — | — | 1 | 1 |
| 4j | 4-CN | 218–220 | 40 | 30 | 30 | 30 | 30 | 300 | 100 | 12.5 | 2 | 4 | 4 | 4 | 4 |
| 5a | 2-F | 228–230 | 42 | 100 | 300 | 300 | — | — | — | 50 | 2 | 4 | 4 | 4 | 4 |
| 5b | 3-F | 209 | 42 | 30 | 300 | 100 | — | 300 | 300 | 50 | 4 | 4 | 4 | 4 | 4 |
| 5c | 2,3-$F_2$ | 225 | 50 | 100 | 100 | 300 | — | — | — | 12.5 | – | 3 | 4 | 4 | 4 |
| 5d | 2,4-$F_2$ | 229–230 | 42 | 30 | 30 | 100 | — | — | — | 50 | 3 | 4 | 4 | 4 | 4 |
| 5e | 2,5-$F_2$ | 230 | 65 | 100 | 300 | 100 | — | 300 | 300 | 12.5 | — | 1 | 1 | 4 | 1 |
| 5f | 2,6-$F_2$ | 232 | 30 | 30 | 30 | 300 | 300 | 300 | 300 | 12.5 | 0 | 2 | 4 | 4 | 4 |
| 5g | 3,4-$F_2$ | 212–213 | 86 | 100 | 30 | 30 | 300 | — | — | 50 | 2 | 4 | 4 | 4 | 4 |
| 5h | 2-Cl | 207–208 | 42 | 30 | 30 | 100 | 300 | 300 | — | 50 | 3 | 4 | 4 | 4 | 4 |
| 5i | 3-Cl | 185–186 | 35 | 30 | 100 | 30 | 300 | 300 | 100 | 50 | — | 4 | 4 | 4 | 3 |
| 5j | 3,4-$Cl_2$ | 216–217 | 45 | 300 | 30 | — | — | — | 300 | 50 | — | 2 | 4 | 4 | 4 |
| 5k | 2-F, 4-Cl | 225–226 | 60 | 30 | 30 | — | — | 100 | 30 | 12.5 | 2 | 4 | 4 | 4 | 4 |
| 5l | 2-Cl, 4-F | 209–210 | 59 | 30 | 30 | — | — | 100 | 300 | 50 | 4 | 4 | 4 | 4 | 4 |
| 5m | 2-Br, 4-F | 203–205 | 40 | 100 | 100 | 300 | — | 300 | 300 | 50 | 4 | 4 | 4 | 4 | 4 |
| 5n | 2-$CH_3$ | 205 | 25 | 30 | 100 | 100 | 100 | 300 | 300 | 12.5 | — | 4 | 3 | 4 | 4 |
| 5o | 3-$CH_3$ | 205–206 | 35 | 30 | 100 | — | — | 100 | 300 | 12.5 | — | 4 | 4 | 3 | 2 |
| 5p | 4-$C_2H_5$ | 210 | 40 | 30 | 30 | 300 | — | 300 | 100 | 12.5 | — | 2 | 4 | 4 | 4 |
| 5q | 4-n-$C_3H_7$ | 215 | 53 | 100 | 100 | 300 | — | — | 300 | 12.5 | — | 1 | 2 | 4 | 2 |
| 5r | 4-n-$C_4H_9$ | 192–193 | 38 | 100 | 30 | — | 100 | 300 | 100 | 12.5 | — | 2 | 2 | 3 | 4 |
| 5s | 4-t-$C_4H_9$ | 200–202 | 48 | 100 | 30 | — | 100 | 100 | 100 | 12.5 | — | — | 4 | 4 | 4 |
| 5t | 4-t-$C_8H_{17}$ | 190 | 30 | — | — | — | — | — | 300 | – | – | – | – | – | – |
| 5u | 4-O-n-$C_4H_9$ | 203 | 35 | 300 | 100 | 300 | 300 | 300 | 300 | 12.5 | — | — | — | — | 2 |
| 5v | 4-O-n-$C_7H_{15}$ | 204–206 | 20 | — | — | — | — | 300 | – | – | – | – | – | – | – |
| | Phenytoin | | | 30 | 30 | — | — | 100 | 100 | – | – | – | – | – | – |
| | Carbamazepine | | | 30 | 100 | 100 | 300 | 100 | 300 | – | – | – | – | – | – |
| | Valproic acid | | | — | — | 300 | — | — | — | – | – | – | – | – | – |

[a]Doses of 30, 100 and 300 mg/kg were administered. The figures in the table indicate the minimum dose whereby bioactivity was demonstrated in half or more of the mice. The animals were examined 0.5 h and 4 h after injections were made. The lines — indicate an absence of anticonvulsant activity and neurotoxicity.

[b]The figures in the screen indicate the number of rats out of 4 which were protected. The lines — mean that no activity was demonstrated and the designation – indicates that the compound was not screened.

The details of the syntheses of the various compounds are indicated below.

Synthesis of Intermediates

The 3-phenoxybenzaldehyde used as a starting material required in the synthesis of compounds 3 was obtained from the Aldrich Chemical Company, Milwaukee, Wis. The intermediate aryloxyaryl aldehydes required in the synthesis of the other compounds were prepared as follows. Anhydrous potassium carbonate (0.12M) was added to a solution of the appropriate phenol (0.15M) and 4-fluorobenzaldehyde (0.14M) in dimethylacetamide (100 mL). The mixture was heated under reflux at 155° C. under nitrogen and the progress was monitored by thin layer chromatography (TLC) using a solvent system of benzene:methanol (9:1 by volume). After approximately 5–10 hours, the mixture was cooled and water (100 mL) was added. The reaction mixture was extracted with chloroform (2·100 mL) and the combined organic extracts were washed with aqueous sodium hydroxide solution (4% w/v) and water. After drying over anhydrous magnesium sulfate, the solvent was removed in vacuo and the resultant oil was distilled under reduced pressure to give the appropriate aryloxyaryl aldehyde. The purity of the distillate was checked by thin layer chromatography (TLC) using benzene:methanol (9:1 by volume) as the solvent. The $^1$H NMR spectrum of a representative intermediate, namely 4-phenoxybenzaldehyde, was as follows: δ($CDCl_3$):9.94(s,1H, CHO), 7.82–7.88 (2t,2H,ortho H of proximal aryl ring), 7.38–7.46 (3t,2H,meta H of proximal aryl ring), 7.20–7.27(3t,1H,para H of distal aryl ring), 7.03–7.12 (3t,4H, ortho and meta H of distal aryl ring).

Synthesis of Final Compounds

A mixture of semicarbazide hydrochloride (0.01M), sodium acetate (0.01M) and water (10 mL) was added slowly to a stirring solution of the aryloxyaryl aldehyde (0.01M) in ethanol (95%, 30 mL). The reaction mixture was stirred at room temperature for 1–2 hours, the precipitate was collected, washed with ether, dried and recrystallized from 95% ethanol (compounds 3, 4b, 4e, 4h, 5b-3, 5k-e, 5v), absolute ethanol (compounds 4a, 4c, 4d, 4g, 4i, 5a, 5fj ,5u) or methanol compound (4f).

The literature melting point (° C.) of compound 4a was 219°–220° C.

The melting points indicated for the various compounds are uncorrected. Elemental analyses (C,H,N) are were within 0.4% of the calculated values except for compound 5n (calcd. for $C_{15}H_{15}N_3O_2$:N,15.60. Found: N, 14.80). $^1$H NMR spectroscopy was undertaken using a BRUKER AM 300 FT (trademark) NMR instrument. Thin layer chromatography (TLC) was performed using silica gel sheets with a fluorescent indicator.

EXAMPLE 2

An initial anticonvulsant evaluation of the compounds prepared according to Example 1 was undertaken by administering the compounds by the intraperitoneal route to mice. Protection and/or neurotoxicity was noted 0.5 and 4 hours after administering doses of 30, 100 and 300 mg/kg of each semicarbazone to the animals. These results are presented in Table 1 above.

All of the compounds were active in the MES screen except compounds 2a,b,5t,v and protection was afforded by 60% of the compounds in the scPTZ test. Neurotoxicity was displayed by approximately 70% of the semicarbazones. Bioactivity was quantitated for selected compounds and these data are given in Table 2 below:

TABLE 2

Evaluation of Selected Compounds in the MES, acPTZ and Neurotoxicity Screens after Intraperitoneal Injection in Mice

| | MES screen | | | acPTZ screen | | | neurotoxicity screen | | | PI | |
|---|---|---|---|---|---|---|---|---|---|---|---|
| Compound | t (h) | $ED_{50}$ (mg/kg) (95% CI) | slope (SE) | t (h) | $ED_{50}$ (mg/kg) (95% CI) | slope (SE) | t (h) | $TD_{50}$(mg/kg) (95% CI) | slope (SE) | $\left(\frac{TD_{50}}{ED_{50}}\right)_{MES}$ | $\left(\frac{TD_{50}}{ED_{50}}\right)_{scPTZ}$ |
| 4b | 1 | 12.86 (10.54–17.09) | 8.28 (3.00) | 1 | >54 | — | 1 | 108.03 (71.52–157.52) | 3.69 (0.96) | 8.40 | — |
| 4f | 1 | 14.65 (10.44–19.23) | 5.59 (1.91) | 1 | 88.55 (45.52–173.94) | 1.87 (0.57) | 2 | 203.73 (132.44–271.13) | 4.29 (1.31) | 13.91 | 2.30 |
| 5a | 0.5 | 20.69 (18.68–22.14) | 18.59 (5.63) | 0.5 | >220 | — | 2 | 170.01 (146.81–191.65) | 12.36 (3.80) | 8.22 | — |
| 5c | 1 | 45.78 (41.39–52.15) | 15.53 (5.71) | 1 | >350 | — | 2 | 292.55 (209.59–379.29) | 5.78 (1.77) | 6.39 | — |
| 5d | 0.25 | 11.25 (6.68–19.16) | 2.78 (0.86) | 0.25 | 57.85 (30.13–93.95) | 1.70 (0.54) | 1 | 96.81 (77.60–113.81) | 11.50 (4.08) | 8.61 | 1.67 |
| 5g | 1 | 14.48 (9.53–18.91) | 4.62 (1.35) | 0.5 | 72.78 (49.01–99.12) | 4.27 (1.34) | 2 | 94.80 (59.86–156.29) | 3.17 (1.09) | 6.55 | 1.30 |
| 5i | 0.5 | 27.69 (20.39–36.12) | 6.01 (2.08) | 0.5 | 41.16 (26.98–56.74) | 3.53 (0.91) | 2 | 64.48 (42.03–84.72) | 4.54 (1.36) | 2.33 | 1.57 |
| 5l | 1 | 13.12 (8.70–20.12) | 3.12 (1.03) | 1 | >68 | — | 1 | 62.46 (55.56–67.86) | 15.48 (4.84) | 4.76 | — |
| 5q | | scheduled | | | | | | | | | |
| 5p | | scheduled | | | | | | | | | |
| 5r | 4 | 13.36 (10.393–16.258 | 6.945 (2.045) | 1 | 86.93 (71.514–108.966) | 11.442 (4.493) | 4 | 131.27 (110.848–158.464) | 6.467 (1.703) | 9.825 | 1.510 |
| 5s | 4 | 8.87 (7.704–4.957) | 13.063 (3.833) | 4 | >150.00 | — | 4 | 105.92 (85.053–142.591) | 6.313 (1.976) | 11.934 | >0.076 |

TABLE 2-continued

Evaluation of Selected Compounds in the MES, acPTZ and Neurotoxicity Screens after Intraperitoneal Injection in Mice

| | MES screen | | | acPTZ screen | | | neurotoxicity screen | | | PI | |
|---|---|---|---|---|---|---|---|---|---|---|---|
| Compound | t (h) | $ED_{50}$ (mg/kg) (95% CI) | slope (SE) | t (h) | $ED_{50}$ (mg/kg) (95% CI) | slope (SE) | t (h) | $TD_{50}$(mg/kg) (95% CI) | slope (SE) | $\left(\frac{TD_{50}}{ED_{50}}\right)_{MES}$ | $\left(\frac{TD_{50}}{ED_{50}}\right)_{scPTZ}$ |
| 5t | 2 | 11.27 (8.313–12.872) | 10.881 (4.272) | 2 | >200 | — | 2 | 124.53 (81.064–175.187) | 3.924 (1.095) | 11.048 | >0.623 |
| Phenytoin | 1 | 6.32 (5.44–7.23) | 11.24 (3.52) | 1 | >50 | — | 0.5 | 41.23 (36.90–46.14) | 14.39 (4.82) | 6.52 | — |
| Carbamazepine | 0.25 | 9.85 (8.77–10.7) | 20.8 (7.15) | 0.25 | >50 | — | 0.25 | 47.8 (39.2–59.2) | 7.98 (2.37) | 4.85 | — |
| Valproate | 0.25 | 287 (237–359) | 7.31 (2.48) | 0.25 | 209 (176–249) | 8.51 (2.69) | 0.25 | 483 (412–571) | 12.3 (4.01) | 1.68 | 2.31 |

The majority of the compounds were examined for oral activity in rats. Initially doses of 50 mg/kg of the semicarbazones were administered. However as the data in Table 1 reveal, with the exception of compound 3, all compounds examined at this dose displayed activity in the MES screen. In an attempt to discern those compounds possessing marked oral activity, the dose was reduced fourfold to 12.5 mg/kg, revealing that protection in the MES screen was retained in all cases. Using the doses indicated in Table 1, neurotoxicity was absent during the 0.25–4 hour time period with the exception of compound 51 in which case ¼ rats caused neurological deficit 1,2 and 4 hours after oral administration. Compounds 4e,5b,d,g-i,n,g,r were evaluated in the scPTZ screen at the doses indicated in Table 1 but they were either inactive (compounds 5b,d,g,i,g) or displayed only marginal activity, details of which are given below. Quantitation of selected compounds was undertaken and the figures obtained are presented in Table 3.

TABLE 3

Evaluation of Selected Compounds in the MES and Neurotoxicity Tests after Oral Administration to Rats

| | MES screen | | | neurotoxicity screen | | | |
|---|---|---|---|---|---|---|---|
| Compound | t (h) | $ED_{50}$(mg/kg) (95% CI) | slope (SE) | t (h) | $TD_{50}$(mg/kg) (95% CI) | slope (SE) | PT[a] |
| 4b | 2 | 1.59 (1.01–2.25) | 3.17 (0.84) | ¼–24[b] | >500 | — | >315 |
| 4f | 2 | 3.43 (2.282–4.726) | 4.121 (1.324) | 2 | >500 | | >145.57 |
| 5c | 4 | 6.15 (3.69–9.71) | 2.55 (0.69) | — | — | — | — |
| 5e | 2 | 11.44 (7.61–15.75) | 4.12 (1.32) | — | — | — | — |
| 5g | 4 | 2.37 (1.54–3.62) | 3.18 (0.81) | ¼–24[b] | >500 | — | >210 |
| 5k | 4 | 1.13 (0.713–2.005) | 2.661 (0.949) | | >90 | | >79.179 |
| 5n | 2 | 5.65 (3.79–7.81) | 3.65 (0.98) | ¼–24[b] | >500 | — | >88 |
| 5o | 1 | 3.07 (2.579–3.944) | 7.114 (2.292) | | >500 | | >162.47 |
| 5p | 6 | 6.48 (2.970–15.536) | 1.98 (0.753) | — | — | — | — |
| 5q | 2 | 2.63 (1.689–3.926) | 3.213 (0.819) | | >500 | | >190.02 |
| 5r | 4 | 3.21 (2.252–4.636) | 3.575 (1.022) | | >3.22 | | >100.16 |
| 5s | 4 | 1.68 (1.146–2.438) | 4.437 (1.281) | | >500 | | >297.24 |
| 5u | 4 | 45.81 (19.481–315.522) | 1.327 (0.524) | | | | |
| Phenytoin | 2 | 23.2 (21.4–25.4) | 15.1 (4.28) | ¼–24[b] | >500 | | >21.6 |

TABLE 3-continued

Evaluation of Selected Compounds in the MES and Neurotoxicity Tests after Oral Administration to Rats

| | MES screen | | | neurotoxicity screen | | | |
|---|---|---|---|---|---|---|---|
| Compound | t (h) | $ED_{50}$(mg/kg) (95% CI) | slope (SE) | t (h) | $TD_{50}$(mg/kg) (95% CI) | slope (SE) | PT[a] |
| Carba-mazepine | 1 | 3.57 (2.41–4.72) | 3.84 (1.15) | 1 | 361 (319–402) | 11.4 (2.96) | 101 |
| Valproate | 0.5 | 395 (332–441) | 8.13 (2.76) | 0.5 | 859 (719–1148) | 6.57 (2.17) | 2.17 |

[a]PI indicates the protection index i.e. $TD_{50}/ED_{50}$.
[b]The compound was examined 0.25, 0.5, 1, 3, 4, 6, 8, and 24 h after administration.

Further bioevaluations of compound 4b were undertaken. After intraperitoneal injection into rats, the $ED_{50}$ and $TD_{50}$ figures in the MES and neurotoxicity screens for 4b were 2.37 and 80.09 mg/kg respectively revealing a PI of 33.8. Using a kindled rat screen, the $ED_{50}$ figure of this compound was 3.93 mg/kg. A daily dose of 100 mg/kg of 4b was administered orally for three days to rats. Afterwards, the livers were removed and comparisons made between the hepatic tissue from treated and control animals, namely liver weights and microsomal protein yields in addition to the enzyme activities of cytochrome P450, p-nitroanisole O-demethylase, UDP-glucuronosyl transferase, sulfotransferase, ethoxyresorfin O-deethylase, pentoxyresorvfin O-dealkylase, glutathione S-transferase and quinone reductase. No differences in the properties between the livers from treated and control livers were detected ($p>0.05$).

Both 4b and 5g were examined for proconvulsant properties in the intravenous pentylenetetrazole test in mice; the doses administered were the MES $ED_{50}$ and the $TD_{50}$ figures of 4b and 5g indicated in Table 2. Neither compound possessed this undesirable feature and using a dose of 108 mg/kg, 4b increased the time to clonus. Compounds 4b and 5g were also evaluated for their ability to prevent convulsions induced by the subcutaneous administration of bicuculline and picrotoxin in mice. The semicarbazone 4b gave partial protection in these two screens whereas 5g was inactive. In addition 4b afforded no protection in the subcutaneous strychnine test in mice.

Full details of these tests are provided below.

Intraperitoneal Injection in Mice

In addition to the information summarized in Table 1, intraperitoneal injection of a number of compounds into mice elicited the following side effects at various doses (mg/kg) and time intervals. First, in the scPTZ screen, myoclonic jerks were noted with the following compounds namely 4c:30,100;0.5h and 5f: 100,300;0.5h. Second continuous seizure activity was observed in the scPTZ screen as follows: 4c:300;0.5h; 100,300;4h; 4d:100,300;0.5 and 4h;4i:100,300;0.5 and 4h;5i:300;0.5h; 51:300,0.5 and 4h;5o:100,300;0.5h and 5s:300;4h. At the end of the 4 hours, continuous seizure activity followed by death resulted in the scPTZ screen when mice received 300 mg/kg of 5o.

Oral Administration to Rats

Using the doses indicated in Table 1, several compounds showed marginal activity in the scPTZ screen. These compounds as well as the number of rats protected at different time periods are as follows: 4e.:1/4 after 0.5,1,4h; 5h:1/4 after 4h; 5n:1/4 after 0.5,1,2h and 5r: 1/4 after 1,4h and 2/4 after 2 hours.

Intraperitoneal Injection of Compound 4b in Rats

The $ED_{50}$ figures, 95% CI values and slope (SE) for 4b in the MES screen obtained 4h after intraperitoneal injection into rats were as follows: 2.37, 1.39–3.57 and 2.65(0.76) while the corresponding $TD_{50}$ data were 80.09,66.14–87.27 and 17.02(6.41). The protection afforded after intraperitoneal administration of 125 and 250 mg/kg of 4b in the scPTZ screen was displayed in 0/2 and 1/10 rats.

Kindled Rat Test Using Compound 4b

The kindled rat test was undertaken by reported procedures (as indicated above). Compound 4b was administered orally and the animals challenged with electrical stimuli 2h later. The $ED_{50}$ is the dose required to reduce seizures from stage 5 to stage 3 or less and these stages are described as follows namely stage 1 is mouth and facial clonus, stage 2 is stage 1 plus head nodding, stage 3 is stage 2 plus forelimb clonus, stage 4 is stage 3 plus rearing and stage 5 is stage 4 plus repeated rearing and falling. The $ED_{50}$ (mg/kg), 95% CI and slope (SE) figures for 4b were as follows: 3.93, 2.40–6.09 and 3.62(1.10). The $ED_{50}$ data (mg/kg, 95% CI in parentheses) and times of the test for three reference drugs were as follows: phenytoin: >100, 0.25 h; carbamazepine: 28.90 (7.72–75.59), 1h and valproate: 117.41 (67.98–189.02), 0.25h.

Effect of Chronic Oral Administration of 4b on Rat Livers

Rats were administered 100 mg/kg of 4b daily for 3 days. The livers were removed, weighed and the effect of 4b on the liver microsomal system were compared to control animals which received only the vehicle (sonicated 0.5% methylcellulose).[21-23]

(VI) Evaluation of 4b and 5g in the Timed Intravenous

Pentylenetetrazole Test

Compounds 4b and 5g in methylcellulose solution (0.5%) were injected intraperitoneally into mice. The two doses used were the approximate $ED_{50}$ values in the MES test and the $TD_{50}$ figures. After 1h, a solution of pentylenetetrazole (0.5%), sodium chloride and sodium heparin (10 USP units/mL) in water were infused into the tail veins of mice at a rate of 0.37 mL/min (4b) and 0.34 mL/min (5g). The times from the commencement-of the infusion until the appearances of the first twitch and also the onset of clonus were recorded for the test and control animals. From these data, the quantities of pentylenetetrazole infused was obtained. Ten animals were used as controls and for each dose administered except for the 13 mg/kg dose of 4b in which case 9 animals were employed. The figures for the times of the first twitch in seconds, quantity of pentylenetetrazole administered in mg/kg (SE) and p values were as follows: 4b(dose of 13 mg/kg): 32.2,32.3(1.4), >0.05;4b(dose of 108 mg/kg):32.2, 32.6(0.8), >0.05; 5g(dose of 15 mg/kg): 32.8,32.9(1.4), >0.05;5g(dose of 95 mg/kg): 34.6,34.6(1.5), >0.05. The relevant data for the times to clonus in seconds, quantity of pentylenetetrazole administered in mg/kg (SE) and p values were as follows: 4b(dose of 13 mg/kg): 37.6, 37.6(1.5), >0.05;4b(dose of 108 mg/kg): 41.5,42.1(1.4), <0.01;5g(15 mg/kg): 41.2,41.2(2.6), 0.05;5g(dose of 95 mg/kg): 44.4, 44.4(2.5), >0.05.

(VII) Evaluation of 4h and 5g Using Other Chemically Induced Seizure Models

Various doses of 4b and 5g were administered to mice 1h (4b) or 0.5 h (5g) before chemoconvulsant doses of bicuculline and picrotoxin were given subcutaneously to mice. Compound 4b was also examined for protective effects after subcutaneous administration of strychnine. In the case of 4b, the number of animals protected in the subcutaneous bicuculline test at different doses (mg/kg) were as follows: 0/8(54), 3/8(108) and 3/8(216). In the subcutaneous picrotoxin test, the protection at various doses (mg/kg) were as follows: 1/8(27), 5/16(108), 2/8(216). Compound 5g showed no effect in the 12–96 mg/kg dose range in these two tests. The semicarbazone 4b afforded no protection in the subcutaneous strychnine test using a dose range of 13.5–108 mg/kg. Two animals per dose were used except in the bicuculline and picrotoxin tests for 4b in which cases, 8 or 16 animals per dose were employed.

EXAMPLE 3

Figure 3:
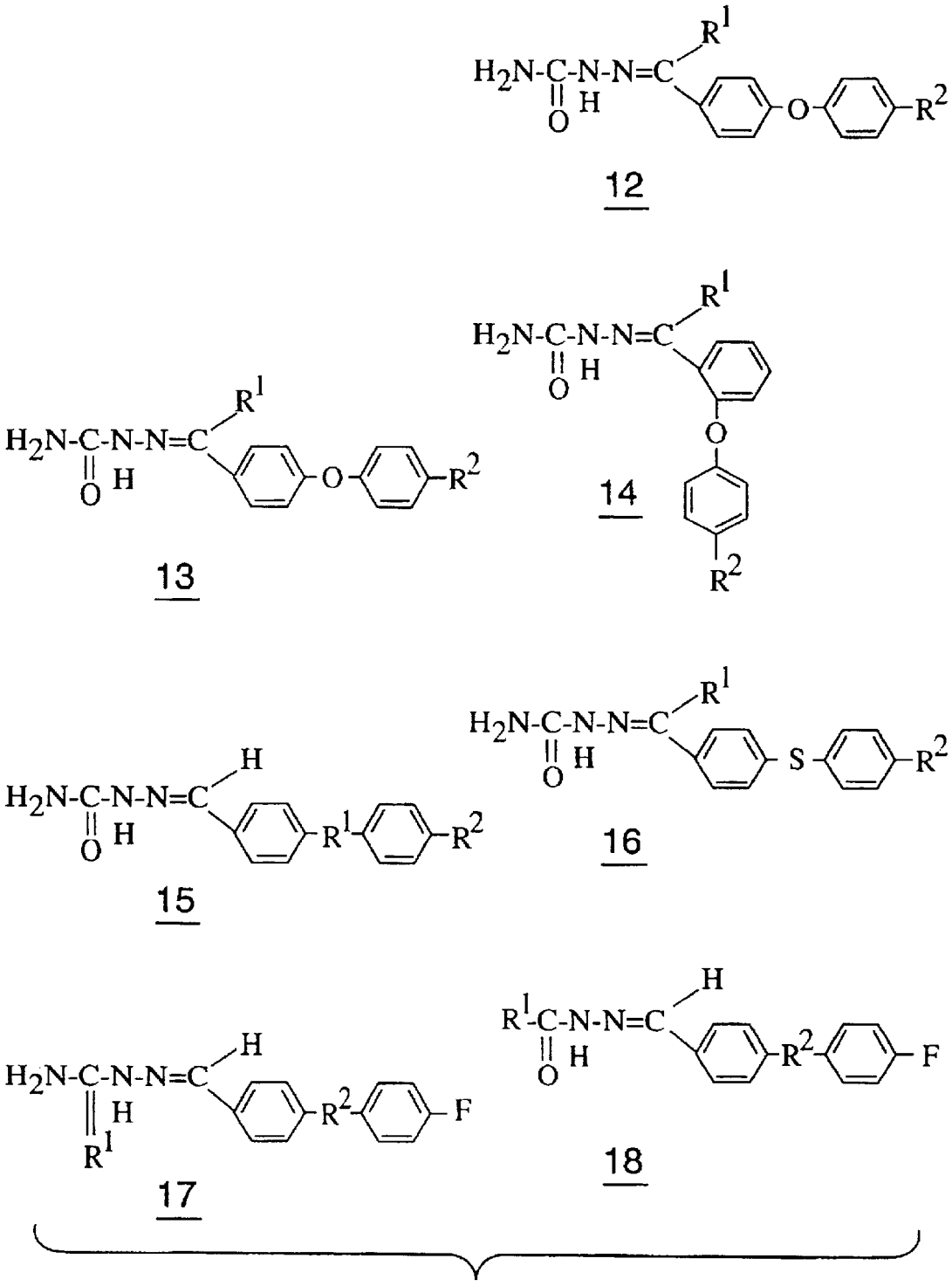
FIG. 3 shows basic chemical structures to indicate the compounds listed in Tables 4 to 6.

The compounds having the structures shown in Table 4 were prepared. The structures of the listed compounds correspond to those shown in FIG. 3 identified by the same first number (12, 13, 14, 15, 16, 17 or 18), with only the substituents being identified in Table 4.

TABLE 4

Aryl Substituents, Physical Data and Anticonvulsant Evaluation after Intraperitoneal Injection into Mice and Oral Administration to Rats of the Compounds in Series 12–18[a]

| | | | | | intraperitoneal injection in mice[b] | | | | | | | oral administration to rats[c] | | | | |
|---|---|---|---|---|---|---|---|---|---|---|---|---|---|---|---|---|
| | | | m.p. | yield | MES screen | | acPTZ screen | | toxicity screen | | dose | MES screen | | | | |
| compound | $R^1$ | $R^2$ | (° C.) | % | 0.5 h | 4 h | 0.5 h | 4 h | 0.5 h | 4 h | (mg/kg) | 0.25 h | 0.5 h | 1 h | 2 h | 4 h |
| 12a | H | F | 240[a] | 65 | 30 | 100 | — | — | — | — | 50 | 2 | 4 | 4 | 4 | 4 |
| 12b | H | H | 224–225 | 60 | 100 | 300 | — | — | — | — | 50 | — | 3 | 4 | 4 | 4 |
| 12c | H | Cl | 225–226 | 40 | 30 | 30 | 30 | — | 300 | 30 | 50 | 4 | 4 | 4 | 4 | 4 |
| 12d | H | Br | 225–226 | 60 | 30 | 30 | — | — | 300 | 30 | 50 | 1 | 4 | 4 | 4 | 4 |
| 12e | H | $CH_3$ | 219–221 | 50 | 30 | 100 | — | — | — | — | 50 | 3 | 4 | 4 | 4 | 4 |
| 13a | $CH_3$ | H | 169–171 | 60 | 30 | 100 | — | — | 100 | 100 | 30 | 4 | 4 | 4 | 4 | 4 |
| 13b | $CH_3$ | F | 182–184 | 74 | 30 | 30 | 100 | — | 300 | 100 | 12.5 | — | 4 | 4 | 4 | 4 |
| 13c | $CH_3$ | Cl | 192–194 | 60 | 30 | 30 | — | 30 | 30 | 100 | 30 | 3 | 4 | 4 | 4 | 4 |
| 13d | $CH_3$ | Br | 195–197 | 30 | 30 | 30 | 300 | — | 300 | 100 | 12.5 | 1 | 3 | 4 | 4 | 4 |
| 13e | $C_2H_5$ | H | 154–156 | 58 | 30 | 100 | — | — | 100 | 100 | 30 | 1 | 4 | 3 | 3 | — |
| 13f | $C_2H_5$ | F | 170–172 | 72 | 30 | 30 | 100 | — | 300 | 100 | 12.5 | — | 2 | 4 | 4 | 4 |
| 13g | $C_2H_5$ | Cl | 186–188 | 38 | 30 | — | 300 | — | 300 | 100 | 30 | — | 1 | 4 | 4 | 4 |
| 13h | $C_2H_5$ | Br | 184–186 | 38 | 30 | 30 | 100 | — | 300 | 100 | 12.5 | — | 2 | 4 | 4 | 4 |
| 14a | $CH_3$ | H | 136–138 | 14 | 300 | — | 300 | — | 300 | — | – | – | – | – | – | – |
| 14b | $CH_3$ | F | 154–157 | 27 | — | — | — | — | — | — | 30 | 1 | 1 | 3 | 3 | 2 |
| 14c | $CH_3$ | Cl | 167–169 | 32 | 300 | 300 | 300 | 300 | 300 | 300 | – | – | – | – | – | – |
| 14d | $CH_3$ | Br | 183–186 | 28 | — | — | — | — | 300 | — | – | – | – | – | – | – |
| 14e | $C_2H_5$ | F | 156–158 | 55 | — | — | — | — | — | 300 | 12.5 | — | — | — | — | — |
| 14f | $C_2H_5$ | Cl | 136–138 | 15 | 300 | 300 | — | — | — | — | – | – | – | – | – | – |
| 14g | $C_2H_5$ | Br | 155–157 | 5 | — | — | — | — | — | 300 | – | – | – | – | – | – |
| 15a | S | H | 226–227 | 40 | 30 | 30 | — | — | — | 300 | 50 | — | 4 | 4 | 4 | 4 |
| 15b | OCO | H | 237–238 | 70 | — | 300 | — | — | — | — | 12.5 | — | — | — | — | — |
| 15c | OCO | Cl | 245–246 | 80 | — | 300 | — | — | — | — | 12.5 | 1 | — | 1 | — | 2 |
| 15d | $OCH_2$ | H | 212–213 | 52 | 300 | 300 | — | 100 | — | — | 12.5 | — | — | 1 | 1 | — |
| 15e | $SO_2$ | H | 254 | 40 | — | 300 | — | — | — | — | – | – | – | – | – | – |
| 15f | $OSO_2$ | H | 146 | 40 | 30 | 30 | 30 | — | 300 | 300 | 12.5 | 1 | 2 | 2 | 4 | 3 |
| 15g | $OSO_2$ | $CH_3$ | 205–207 | 70 | — | — | — | — | — | — | — | — | — | — | — | — |
| 16a | H | F | 230–231 | 52 | 30 | 30 | 30 | — | 300 | 100 | 12.5 | 1 | 3 | 4 | 4 | 4 |
| 16b | H | Cl | 216 | 40 | 100 | 30 | 300 | — | — | 100 | 50 | 1 | 4 | 4 | 4 | 4 |
| 16c | H | Br | 212–213 | 30 | 100 | 30 | — | 300 | — | 300 | 12.5 | 0 | 1 | 3 | 4 | 4 |
| 16d | H | $CH_3$ | 225–227 | 32 | 30 | 30 | 100 | 100 | 300 | 100 | 12.5 | 0 | 0 | 4 | 4 | 4 |
| 16e | $CH_3$ | H | 208–210 | 60 | 100 | 100 | 300 | — | — | — | 30 | 0 | 4 | 4 | 4 | 4 |
| 16f | $CH_3$ | F | 204–207 | 91 | 100 | 30 | — | 300 | 300 | 300 | 30 | 3 | 4 | 4 | 4 | 4 |
| 16g | $C_2H_5$ | H | 131–133 | 16 | 30 | 30 | 100 | 100 | 100 | 100 | 30 | — | 3 | 4 | 3 | 4 |
| 16h | $C_2H_5$ | F | 150–157 | 18 | 30 | 100 | — | — | 100 | 100 | 30 | 0 | 0 | 2 | 3 | 3 |
| 17a | S | O | 167 | 56 | 30 | 30 | 30 | 30 | 100 | 30 | 12.5 | — | 2 | 2 | 3 | 1 |
| 17b | NH | O | 181–183 | 50 | 300 | 30 | 30 | — | 100 | 100 | 12.5 | — | — | — | 1 | 2 |
| 17c | S | S | 171–172 | 62 | 100 | 100 | 100 | 100 | — | 100 | 12.5 | — | 1 | 2 | 1 | 1 |
| 17d | NH | S | 172–173 | 40 | 300 | — | 30 | 30 | 100 | 100 | 12.5 | — | — | — | 1 | — |
| 18a | H | O | 176–178 | 60 | 300 | 300 | — | 300 | — | 300 | – | – | – | – | – | – |
| 18b | $CH_3$ | O | 160 | 83 | 30 | 30 | 100 | 100 | 100 | 100 | 12.5 | 1 | 4 | 2 | 2 | 1 |

TABLE 4-continued

Aryl Substituents, Physical Data and Anticonvulsant Evaluation after Intraperitoneal Injection into Mice and Oral Administration to Rats of the Compounds in Series 12–18[a]

| | | | | | intraperitoneal injection in mice[b] | | | | | | | oral administration to rats[c] | | | | |
|---|---|---|---|---|---|---|---|---|---|---|---|---|---|---|---|---|
| | | | m.p. | yield | MES screen | | acPTZ screen | | toxicity screen | | dose | MES screen | | | | |
| compound | $R^1$ | $R^2$ | (° C.) | % | 0.5 h | 4 h | 0.5 h | 4 h | 0.5 h | 4 h | (mg/kg) | 0.25 h | 0.5 h | 1 h | 2 h | 4 h |
| 18c | $NHNH_2$ | O | 220 | 80 | 300 | 100 | — | 300 | — | 300 | 30 | — | — | — | — | — |
| 18d | $CONH_2$ | O | 253 | 75 | — | — | — | — | 300 | 300 | — | — | — | — | — | — |
| 18e | H | S | 146–148 | 80 | 100 | 100 | — | 300 | — | 300 | 30 | 1 | — | — | — | 1 |
| Phenytoin | | | – | – | 30 | 30 | — | — | 100 | 100 | – | – | – | – | – | – |
| Carbamazepine | | | – | – | 30 | 100 | 100 | 300 | 100 | 300 | – | – | – | – | – | – |
| Valproate | | | – | – | — | — | 300 | — | — | — | – | – | – | – | – | – |

[a]Doses of 30, 100 and 300 mg/kg were administered. The figures in the table indicate the minimum dose whereby bioactivity was demonstrated in half or more of the mice. The animals were examined 0.5 h and 4 h after injections were made. The lines — indicate an absence of anticonvulsant activity and neurotoxicity.
[b]The figures in the table indicate the number of rats out of 4 which were protected. The lines — mean that no activity was demonstrated while the designation – reveals that the compound was not screened.

These compounds were synthesized as follows, although attempts to isolate 2-phenoxypropiophenone, required in the synthesis of compound 4 ($R^1$=$C_2H_5$;$R^2$=H), were unsuccessful; the reactions invariably leading to the formation of a number of compounds. The intermediate aldehydes and ketones were reacted with semicarbazide (13–16), thiosemicarbazide (17a,c), aminoguanidine (17b,d), formic acid hydrazide (18a,e), acetic hydrazide (18b), carbohydrazide (18c) or oxamic hydrazide (18d).

Initial anticonvulsant evaluation of compounds 13–18 was undertaken as follows. Doses of 30, 100 and 300 mg/kg were injected by the intraperitoneal route into mice and evaluated in the MES, scPTZ and neurotoxicity screens one half and four hours after administration. The results are presented in Table 4 above in addition to the data for 12a–e which is included for comparative purposes.

Quantitation of the activity of selected compounds was undertaken and these results are indicated in Table 5.

TABLE 5

Quantitation of the Activity of Certain Compounds in the MES, acPTZ and Neurotoxicity Screens after Intraperitoneal Injection in Mice

| | MES screen | | | acPTZ screen | | | neurotoxicity screen | | | PI* | |
|---|---|---|---|---|---|---|---|---|---|---|---|
| Compound | t (h) | $ED_{50}$(mg/kg) (95% CI) | slope (SE) | t (h) | $ED_{50}$(mg/kg) (95% CI) | slope (SE) | t (h) | $TD_{50}$(mg/kg) (95% CI) | slope (SE) | MES | acPTZ |
| 12a | 1 | 12.86 (10.54–17.09) | 8.28 (3.00) | 1 | >54 — | — — | 1 | 108.03 (71.52–157.52) | 3.69 (0.96) | 8.40 | — |
| 13a | 0.25 | 9.08 (6.45–11.31) | 6.21 (1.91) | 0.25 | 43.31 (18.36–112.07) | 1.54 (0.57) | 1 | 73.48 (64.32–86.40) | 10.51 (3.08) | 8.09 | 1.70 |
| 13b | 1 | 11.63 (10.96–12.48) | 22.69 (9.34) | 0.25 | >80 — | — — | 2 | 60.74 (58.92–63.84) | 45.21 (14.45) | 5.22 | — |
| 13f | 1 | 5.46 (4.57–6.46) | 11.64 (3.74) | 2 | 12.84 (8.25–18.55) | 3.34 (1.16) | 2 | 35.26 (25.02–43.44) | 6.78 (2.05) | 6.45 | 2.75 |
| 13g | 4 | 11.09 (10.367–12.583) | 20.278 (6.827) | | | | | <100 | | <9.017 | |
| 15a | 1 | 15.62 (10.45–20.56) | 4.50 (1.36) | 1 | >46 — | — — | 2 | 181.00 (122.53–250.73) | 4.59 (1.27) | 11.59 | — |
| 15f | 0.5 | 25.27 (2.150–29.87) | 9.52 (3.00) | 0.5 | >100 — | — — | 1 | 113.00 (103.0–122.68) | 17.38 (5.73) | 4.47 | — |
| 16a | 1 | 12.37 (9.247–16.128) | 6.372 (1.915) | 1 | >120 | | 2 | 88.00 (83.311—94.847) | 24.001 (6.853) | 7.112 | <0.733 |
| 16b | 1 | 16.22 (14.63–17.59) | 23.21 (8.59) | 1 | >120 — | — — | 2 | 53.18 (41.42–72.54) | 5.90 (1.89) | 3.28 | — |
| 16c | 2 | 24.37 (18.45–30.93) | 5.92 (1.72) | 2 | >200 — | — — | 2 | 122.57 (101.63–149.51) | 6.92 (2.10) | 5.03 | — |
| 16d | 1 | 9.46 (6.353–13.026) | 3.676 (0.986) | 1 | >300 | | 4 | 196.52 (174.429–226.477) | 12.821 (3.957) | 20.776 | <0.655 |
| Phenytoin | 2 | 6.48 (5.66–7.24) | 12.4 (3.60) | 2 | >50 — | — — | 0.5 | 42.8 (36.4–47.5) | 10.2 (3.13) | 6.60 | — |
| Carbamazepine | 0.25 | 9.85 (8.77–10.7) | 20.8 (7.15) | 0.25 | >50 — | — — | 0.25 | 47.8 (39.2–59.2) | 7.98 (2.37) | 4.85 | — |
| Valproate | 0.25 | 287 (237–359) | 7.31 (2.48) | 0.25 | 209 (176–249) | 8.51 (2.69) | 0.25 | 483 (412–571) | 12.3 (4.01) | 1.68 | 2.31 |

*The protection index (PI) is obtained by dividing the $TD_{50}$ figues by the $ED_{50}$ values.

Evaluation of most of the semicarbazones and analogs in the MES and neurotoxicity tests after oral administration to rats was performed. At the doses indicated in Table 4, neurotoxicity was absent and some of the compounds examined in the scPTZ screen were either inactive or afforded only minimal protection. Hence only the MES data are presented in Table 4. The $ED_{50}$ figures of several compounds in the rat oral MES screen are given in Table 6.

TABLE 6

Quantitation of the Activity of Selected Compounds in the MES and Neurotoxicity Screens after Oral Administration to Rats

| | MES Screen | | | Neurotoxicity screen | | | |
|---|---|---|---|---|---|---|---|
| Compound | t (h) | $ED_{50}$(mg/kg) (95% CI) | slope (SE) | t(h) | $TD_{50}$(mg/kg) (95% CI) | slope (SE) | PI[a] |
| 12a[b] | 2 | 1.59 (1.01–2.25) | 3.17 (0.84) | ¼–24[c] | >500 — | — — | >315 |
| 13a | 4 | 9.73 (6.440–14.141) | 3.844 (1.300) | — | — | — | — |
| 13b | 2 | 3.37 (2.37–4.72) | 5.74 (1.80) | 2 | 108.77 (80.26–177.74) | 4.82 (1.82) | 32.3 |
| 13c | 4 | 2.92 (2.203–3.464) | 5.774 (1.595) | 4 | <500 | — | <170.73 |
| 13d | 4 | 1.52 (0.989–2.300) | 3.600 (1.024) | — | >500 | | >328.28 |
| 13e | 0.5 | 23.08 (14.33–36.64) | 3.14 (0.92) | — | — — | — — | — |
| 13f | 2 | 4.25 (2.89–5.97) | 3.67 (1.04) | 4 | >72(<240) — | ->16.9 — | (<56.436) |
| 13g | 2 | 2.89 (1.568–5.294) | 2.035 (0.594) | 0 | >500 | — | >172.81 |
| 13h | 4 | 4.39 (2.67–5.833) | 4.206 (1.279) | | | | |
| 14b | 2 | 43.37 (25.078–66.343) | 2.287 (0.569) | | | | |
| 15a | 4 | 4.29 (3.20–5.24) | 6.02 (2.00) | ¼–24 | >496 — | — — | >115.6 |
| 16a | 2 | 4.98 (3.24–7.01) | 3.92 (1.10) | 4 | 183.05 (100.59–338.35) | 2.49 (0.86) | 36.8 |
| 16f | 2 | 9.11 (6.185–11.658) | 5.285 (1.496) | — | — | — | — |
| 16g | 2 | 18.58 (14.195–25.038) | 5.238 (1.674) | — | — | — | — |
| 18b | 0.5 | 18.66 (12.40–27.60) | 3.93 (1.11) | 2 — | >125 — | — — | >6.70 |
| Phenytoin | 2 | 23.2 (21.4–25.4) | 15.1 (4.28) | ¼–24[c] | >500 — | — — | >21.6 |
| Carbamazepine | 1 | 3.57 (2.41–4.72) | 3.84 (1.15) | 1 | 361 (319–402) | 11.4 (2.96) | 101 |
| Valproate | 0.5 | 395 (332–441) | 8.13 (2.76) | 0.5 | 859 (719–1148) | 6.57 (2.17) | 2.17 |

[a]The letters PI refer to the protection index viz $TD_{50}/ED_{50}$.
[b]Data for this compound were taken from reference 1.
[c]The compound was examined 0.25, 0.5, 1, 2, 4, 6, 8 and 24 h after administration.

The final pharmacological evaluation of representative compounds was undertaken using an epileptic chicken model.[6] In this case, the convulsions which are induced by intermittent photic stimulations have been shown to be prevented by a number of anticonvulsants at blood levels similar to those used in humans. Two series of compounds were examined with the aim of observing whether oxygen or sulfur is a preferable spacer atom between the two aryl rings and also to compare the $ED_{50}$ figures with those obtained in the rat oral and mouse intraperitoneal screens. The $ED_{50}$ values of the ethers 12a–d were 1.5, 2.5, 1.0 and 2.0 mg/kg respectively and for the thioethers bearing the same aryl substitution pattern namely 16a,15a,16b,c, the figures were 1.5, 2.5, 1.0 and 1.5 mg/kg respectively. Hence potencies are unaffected by whether oxygen or sulfur are used as the spacer group. The $ED_{50}$ values of 12a,15a,16a in the rat oral screen are in the 1–5 mg/kg range whereas for 12a,15a,16b,c the figures in the mouse intraperitoneal test are approximately 15–25 mg/kg. Hence the results from the epileptic chicken model are comparable with the data provided in the rat oral screen.

What we claim is:

[1. A compound of the general formula I:

(I)

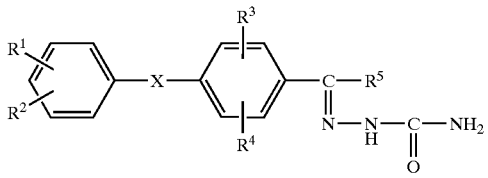

wherein $R^1$, $R^2$, $R^3$ and $R^4$ may be the same or different and each represents hydrogen, halo, $C_{1-9}$alkyl, $C_{3-9}$cycloalkyl, cyano, $C_{1-9}$alkoxy or $C_{6-10}$aryloxy; $R^5$ represents hydrogen, $C_{1-9}$alkyl, $C_{3-9}$cycloalkyl or $C_{6-10}$aryl; and X is oxygen or sulfur; with the proviso that:

a) if X is sulfur, then at least one of $R^1$ and $R^2$ is other than hydrogen or at least one of $R^3$ and $R^4$ is fluoro, $C_{1-9}$alkyl, $C_{3-9}$cycloalkyl, cyano, $C_{1-9}$alkoxy or $C_{6-10}$aryloxy; and b) if X is oxygen, $R^5$ is hydrogen, methyl, or ethyl, and if one of $R^1$ and $R^2$ is chloro or methoxy or if one of $R^3$ and $R^4$ is methyl, then the other of $R^1$ and $R^2$ or the other of $R^3$ and $R^4$ is other than hydrogen; and c) if X is oxygen, $R^5$ is hydrogen, methyl or ethyl, and if $R^1$ and $R^2$ are both hydrogen, then at least one of $R^3$ and $R^4$ is other than hydrogen and methyl;

or a pharmaceutically acceptable salt thereof.]

[2. A compound according to claim 1 wherein at least one of $R^1$ and $R^2$ represents fluoro, $R^3$ and $R^4$ are each hydrogen, $R^5$ is hydrogen or $C_{1-3}$alkyl, and X is O.]

[3. A compound according to claim 1 wherein at least one of $R^1$ and $R^2$ represent fluoro, $R^5$ is hydrogen, and X represents oxygen.]

[4. 4-(4'-Fluorophenoxy)benzaldehyde semicarbazone or a pharmaceutically-acceptable salt thereof.]

5. A method of preparing a compound of [general] formula I:

(I)

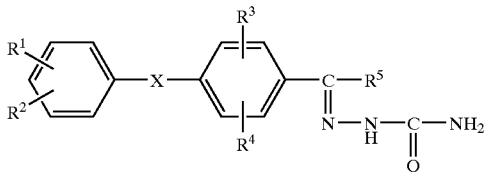

wherein: $R^1$, $R^2$, $R^3$ and $R^4$ may be the same or different and each represents a hydrogen or halogen atom, or a $C_{1-9}$alkyl, $C_{3-9}$cycloalkyl, cyano, $C_{1-9}$alkoxy or $C_{6-10}$aryloxy group; $R^5$ represents a hydrogen atom or a $C_{1-9}$alkyl, $C_{3-9}$cycloalkyl or $C_{6-10}$aryl group; and X is oxygen or sulfur; [except that $R^1$, $R^2$, $R^3$, $R^4$ and $R^5$ may not all be hydrogen;] *with the provisos that:*

(*a*) *if X is sulfur, then at least one of $R^1$ and $R^2$ is other than hydrogen or at least one of $R^3$ and $R^4$ is fluoro, $C_{1-9}$alkyl, $C_{3-9}$cycloalkyl, cyano, $C_{1-9}$alkoxy or $C_{6-10}$aryloxy; and*

(*b*) *if X is oxygen, and $R^5$ is hydrogen, methyl, or ethyl, and one of $R^1$ and $R^2$ is chloro, then* (*i*) *the other of $R^1$ and $R^2$ is other than hydrogen or chloro, or* (*ii*) *at least one of $R^3$ and $R^4$ is other than hydrogen; and*

(*c*) *if X is oxygen, and $R^5$ is hydrogen, methyl, or ethyl, and one of $R^1$ and $R^2$ is methoxy, then* (*i*) *the other of $R^1$ and $R^2$ is other than hydrogen or methoxy, or* (*ii*) *at least one of $R^3$ and $R^4$ is other than hydrogen; and*

(*d*) *if X is oxygen, and $R^5$ is hydrogen, methyl, or ethyl, and one of $R^1$ and $R^2$ is methyl, then* (*i*) *the other of $R^1$ and $R^2$ is other than hydrogen or* (*ii*) *at least one of $R^3$ and $R^4$ is other than hydrogen; and*

(*e*) *if X is oxygen, $R^5$ is hydrogen, methyl or ethyl, and $R^1$ and $R^2$ are both hydrogen, then at least one of $R^3$ and $R^4$ is other than hydrogen and methyl;* which method comprises forming an intermediate aryloxy- or arylthio-benzaldehydes or ketones by reacting a corresponding (thio)phenol with fluorobenzaldehyde or a fluoroaryl ketone in a solvent in the presence of potassium carbonate at temperatures in the range of 100° to 200° C. under a non-oxidizing gas, extracting the intermediate and then reacting the intermediate with semicarbazide and collecting the resulting precipitate of the desired compound.

6. A method of treating a human or animal patient for a disorder of the central nervous system, comprising administering to said patient an effective amount of a compound having the general formula I:

(I)

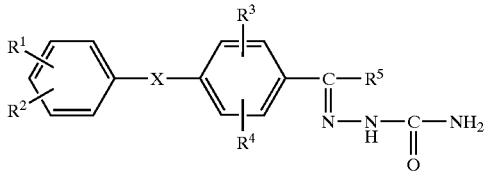

wherein: $R^1$, $R^2$, $R^3$ and $R^4$ may be the same or different and each represents hydrogen, halo, $C_{1-9}$alkyl, $C_{3-9}$cycloalkyl, cyano, $C_{1-9}$alkoxy or $C_{6-10}$aryloxy; $R^5$ represents hydrogen, $C_{1-9}$alkyl, $C_{3-9}$cycloalkyl or $C_{6-10}$aryl; and X is oxygen or sulfur; with the proviso that[;]:

a) at least one of $R^1$, $R^2$, $R^3$ or $R^4$ is other than hydrogen, or b) $R^5$ is other than hydrogen, methyl and ethyl;

or a pharmaceutically acceptable salt thereof.

7. A method according to claim 6 wherein said disorder exhibits convulsions or seizures.

8. A method according to claim 6 wherein said disorder exhibits epileptic seizures.

[9. A compound of claim 1 which is selected from the group consisting of 4-(4-bromophenoxy)benzaldehyde semicarbazone; 4-(4-iodophenoxy)benzaldehyde semicarbazone; 4-(4-methylphenoxy)benzaldehyde semicarbazone; 4-(4-cyanophenoxy)benzaldehyde semicarbazone; 4-(2-fluorophenoxy)benzaldehyde semicarbazone; 4-(3-fluorophenoxy)benzaldehyde semicarbazone; 4-(2,3-difluorophenoxy)benzaldehyde semicarbazone; 4-(2,4-difluorophenoxy)benzaldehyde semicarbazone; 4-(2,5-difluorophenoxy)benzaldehyde semicarbazone; 4-(2,6-difluorophenoxy)benzaldehyde semicarbazone; 4-(3,4-difluorophenoxy)benzaldehyde semicarbazone; 4-(3,4-dichlorophenoxy)benzaldehyde semicarbazone; 4-(4-chloro-2-fluorophenoxy)benzaldehyde semicarbazone; 4-(2-chloro-4-fluorophenoxy)benzaldehyde semicarbazone; 4-(2-bromo-4-fluorophenoxy)benzaldehyde semicarbazone; 4-(2-methylphenoxy)benzaldehyde semicarbazone; 4-(3-methylphenoxy)benzaldehyde semicarbazone; 4-(4-ethylphenoxy)benzaldehyde semicarbazone; 4-(4-n-propylphenoxy)benzaldehyde semicarbazone; 4-(4-s-butylphenoxy)benzaldehyde semicarbazone; 4-(4-t-butylphenoxy)benzaldehyde semicarbazone; 4-(4-fluorophenoxy)acetophenone semicarbazone; 4-(4-bromophenoxy)acetophenone semicarbazone; 4-(4-fluorophenoxy)propiophenone semicarbazone; 4-(4-bromophenoxy)propiophenone semicarbazone; 4-(4-fluorophenylmercapto)benzaldehyde semicarbazone; 4-(4-chlorophenylmercapto)benzaldehyde semicarbazone; 4-(4bromophenylmercapto)benzaldehyde semicarbazone; 4-(4-methylphenylmercapto)benzaldehyde semicarbazone; and 4(4-fluorophenylmercapto)acetophenone semicarbazone.]

[10. A composition comprising the compound of any one of claims 1–4 and 9, and a pharmaceutically acceptable diluent, excipient or carrier.]

[11. A method of treating a human or animal patient for a disorder of the central nervous system comprising administering to said patient an effective amount of a compound of any one of claims 1–4 and 9, or a pharmaceutically acceptable salt thereof.]

[12. A method according to claim 11, wherein said disorder exhibits convulsions or seizures.]

[13. A method according to claim 12, wherein said disorder exhibits epileptic seizures.]

14. A method according to claim 6, wherein said compound is administered as part of a composition comprising a pharmaceutically acceptable carrier.

[15. A method according to claim 11, wherein said compound is administered as part of a composition comprising a pharmaceutically acceptable carrier.]

*16. A method according to claim 6, wherein X is oxygen.*

*17. A method according to claim 6, wherein one of $R^1$ and $R^2$ is halogen, and the other of $R^1$ and $R^2$ is hydrogen or halogen, $R^3$ and $R^4$ are each hydrogen, $R^5$ is hydrogen or $C_{1-3}$alkyl, and X is O or S.*

*18. A method according to claim 17, wherein at least one of $R^1$ and $R^2$ is fluoro.*

*19. A method according to claim 17, wherein X is O.*

*20. A method according to claim 6, wherein said compound possesses an $ED_{50}$ from 1 to 5 mg/kg in a maximal electroshock screen in rate.*

*21. The method according to claim 20, wherein said compound possesses an $ED_{50}$ from 2 to 3 mg/kg in a maximal electroshock screen in rats.*

*22. A compound of general formula I:*

(I)

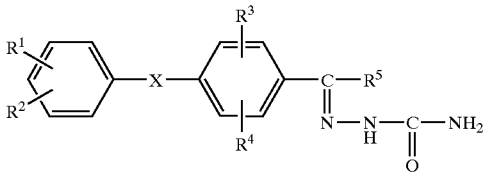

*or a pharmaceutically acceptable salt thereof, wherein:*

*$R^1$ and $R^2$ are independently hydrogen or halogen;*

*$R^3$ and $R^4$ are each hydrogen;*

*$R^5$ is hydrogen or $C_{1-3}$alkyl; and*

*X is O or S;*

*provided that $R^1$ and $R^2$ are not both hydrogen, $R^1$ and $R^2$ do not consist of hydrogen and chloro, and $R^1$ and $R^2$ are not both chloro.*

*23. A compound according to claim 22, wherein X is O.*

*24. A compound according to claim 22, wherein at least one of $R^1$ and $R^2$ is fluoro.*

*25. A compound according to claim 22, wherein $R^5$ is hydrogen.*

*26. A compound selected from the group consisting of:*

*4-(4-bromophenoxy)benzaldehyde semicarbazone; and*

*4-(4-iodophenoxy)benzaldehyde semicarbozone;*

*or a pharmaceutically acceptable salt thereof.*

*27. A compound selected from the group consisting of:*

*4-(2-fluorophenoxy)benzaldehyde semicarbazone;*

*4-(3-fluorophenoxy)benzaldehyde semicarbazone;*

*4-(2,3-difluorophenoxy)benzaldehyde semicarbazone;*

*4-(2,4-difluorophenoxy)benzaldehyde semicarbazone;*

*4-(2,5-difluorophenoxy)benzaldehyde semicarbazone;*

*4-(2,6-difluorophenoxy)benzaldehyde semicarbazone; and*

*4-(3,4-difluorophenoxy)benzaldehyde semicarbazone;*

*or a pharmaceutically acceptable salt thereof.*

*28. A compound selected from the group consisting of:*

*4-(4-chloro-2-fluorophenoxy)benzaldehyde semicarbazone;*

*4-(2-chloro-4-fluorophenoxy)benzaldehyde semicarbazone; and*

*4-(2-bromo-4-fluorophenoxy)benzaldehyde semicarbazone;*

*or a pharmaceutically acceptable salt thereof.*

*29. A compound selected from the group consisting of:*

*4-(4-fluorophenoxy)acetophenone semicarbazone;*

*4-(4-bromophenoxy)acetophenone semicarbazone;*

*4-(4-fluorophenoxy)propiophenone semicarbazone;*

*4-(4-bromophenoxy)propiophenone semicarbazone;*

*4-(4-fluorophenylmercapto)benzaldehyde semicarbazone;*

*4-(4-bromophenylmercapto)benzaldehyde semicarbazone; and*

*4-(4-fluorophenylmercapto)acetophenone semicarbazone;*

*or a pharmaceutically acceptable salt thereof.*

*30. A compound of general formula I:*

(I)

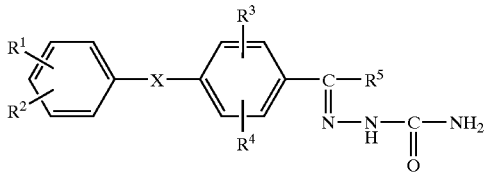

*or a pharmaceutically acceptable salt thereof, wherein:*

*$R^1$, $R^2$, $R^3$ and $R^4$ are independently hydrogen or halogen;*

*$R^5$ is hydrogen; and*

*X is O;*

*provided that $R^1$ and $R^2$ are not both hydrogen.*

*31. The compound 4-(4-chlorophenoxy)benzaldehyde semicarbazone or a pharmaceutically-acceptable salt thereof.*

*32. A compound of formula I:*

(I)

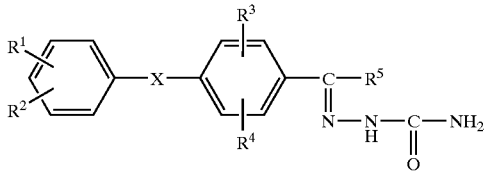

*or a pharmaceutically acceptable salt thereof, wherein*

*$R^1$, $R^2$, $R^3$ and $R^4$ may be the same or different and each represents hydrogen, halo, $C_{1-9}$alkyl, $C_{3-9}$cycloalkyl, cyano, $C_{1-9}$alkoxy or $C_{6-10}$aryloxy;*

*$R^5$ represents hydrogen, $C_{1-9}$alkyl, $C_{3-9}$cycloalkyl or $C_{6-10}$aryl; and*

*X is oxygen or sulfur;*

*with the provisos that:*

*(a) if X is sulfur, then at least one of $R^1$ and $R^2$ is other than hydrogen or at least one of $R^3$ and $R^4$ is fluoro, $C_{1-9}$alkyl, $C_{3-9}$cycloalkyl, cyano, $C_{1-9}$alkoxy or $C_{6-10}$aryloxy; and*

*(b) if X is oxygen, and $R^5$ is hydrogen, methyl, or ethyl, and one of $R^1$ and $R^2$ is chloro, then (i) the other of $R^1$*

*and $R^2$ is other than hydrogen or chloro, or (ii) at least one of $R^3$ and $R^4$ is other than hydrogen; and*

*(c) if X is oxygen, and $R^5$ is hydrogen, methyl, or ethyl, and one of $R^1$ and $R^2$ is methoxy, then (i) the other of $R^1$ and $R^2$ is other than hydrogen or methoxy, or (ii) at least one of $R^3$ and $R^4$ is other than hydrogen; and*

*(d) if X is oxygen, and $R^5$ is hydrogen, methyl, or ethyl, and one of $R^1$ and $R^2$ is methyl, then (i) the other of $R^1$ and $R^2$ is other than hydrogen or (ii) at least one of $R^3$ and $R^4$ is other than hydrogen; and*

*(e) if X is oxygen, $R^5$ is hydrogen, methyl or ethyl, and $R^1$ and $R^2$ are both hydrogen, then at least one of $R^3$ and $R^4$ is other than hydrogen and methyl.*

*33. A compound according to claim 32, wherein at least one of $R^1$ and $R^2$ represents fluoro, $R^3$ and $R^4$ are each hydrogen, $R^5$ is hydrogen or $C_{1-3}$alkyl, and X is oxygen.*

*34. A compound according to claim 32, wherein at least one of $R^1$ and $R^2$ represent fluoro, $R^5$ is hydrogen, and X represents oxygen.*

*35. 4-(4-Fluorophenoxy)benzaldehyde semicarbazone or a pharmaceutically acceptable salt thereof.*

*36. The compound of claim 32, wherein said compound is selected from the group consisting of:*

*4-(4-bromophenoxy)benzaldehyde semicarbazone;*

*4-(4-iodophenoxy)benzaldehyde semicarbazone;*

*4-(4-cyanophenoxy)benzaldehyde semicarbazone;*

*4-(2-fluorophenoxy)benzaldehyde semicarbazone;*

*4-(3-fluorophenoxy)benzaldehyde semicarbazone;*

*4-(2,3-difluorophenoxy)benzaldehyde semicarbazone;*

*4-(2,4-difluorophenoxy)benzaldehyde semicarbazone;*

*4-(2,5-difluorophenoxy)benzaldehyde semicarbazone;*

*4-(2,6-difluorophenoxy)benzaldehyde semicarbazone;*

*4-(3,4-difluorophenoxy)benzaldehyde semicarbazone;*

*4-(4-chloro-2-fluorophenoxy)benzaldehyde semicarbazone;*

*4-(2-chloro-4-*fluorophenoxy)*benzaldehyde semicarbazone;*

*4-(2-bromo-4-*fluorophenoxy)*benzaldehyde semicarbazone;*

*4-(4-ethylphenoxy)benzaldehyde semicarbazone;*

*4-(4-n-propylphenoxy)benzaldehyde semicarbazone;*

*4-(4-s-butylphenoxy)benzaldehyde semicarbazone;*

*4-(4-t-butylphenoxy)benzaldehyde semicarbazone;*

*4-(4-fluorophenoxy)acetophenone semicarbazone;*

*4-(4-bromophenoxy)acetophenone semicarbazone;*

*4-(4-fluorophenoxy)propiophenone semicarbazone;*

*4-(4-bromophenoxy)propiophenone semicarbazone;*

*4-(4-fluorophenylmercapto)benzaldehyde semicarbazone;*

*4-(4-chlorophenylmercapto)benzaldehyde semicarbazone;*

*4-(4-bromophenylmercapto)benzaldehyde semicarbazone;*

*4-(4-methylphenylmercapto)benzaldehyde semicarbazone; and*

*4-(4-fluorophenylmercapto)benzaldehyde semicarbazone.*

*37. 4-(3,4-Dichlorophenoxy)benzaldehyde semicarbazone or a pharmaceutically acceptable salt thereof.*

*38. A compound selected from the group consisting of:*

*4-(2-methylphenoxy)benzaldehyde semicarbazone;*

*4-(3-methylphenoxy)benzaldehyde semicarbazone; and*

*4-(4-methylphenoxy)benzaldehyde semicarbazone;*

*or a pharmaceutically acceptable salt thereof.*

*39. A composition comprising the compound of any one of claims 32–38 and a pharmaceutically acceptable diluent, excipient or carrier.*

*40. A method of treating a human or animal patient for a disorder of the central nervous system comprising administering to said patient an effective amount of a compound of any one of claims 32–38, or a pharmaceutically acceptable salt thereof.*

*41. A method according to claim 40, wherein said disorder exhibits convulsions or seizures.*

*42. A method according to claim 41, wherein said disorder exhibits epileptic seizures.*

*43. A method according to claim 40, wherein said compound is administered as part of a composition comprising a pharmaceutically acceptable carrier.*

*44. The method of claim 5, wherein said method comprises:*

*(i) forming an intermediate aryloxy- or arylthio-benzaldehyde or ketone by reacting a corresponding (thio)phenol with fluorobenzaldehyde or a fluoroaryl ketone in a solvent in the presence of potassium carbonate at temperatures in the range of 100° to 200° C. under nitrogen;*

*(ii) monitoring for formation of said intermediate by thin layer chromatography;*

*(iii) adding water to the solvent containing said intermediate;*

*(iv) partitioning the intermediate into chloroform to form an intermediate solution;*

*(v) washing the intermediate solution with dilute aqueous sodium hydroxide;*

*(vi) drying the washed intermediate solution over anhydrous magnesium sulfate;*

*(vii) removing the chloroform from the dried and washed intermediate solution by solvent evaporation under vacuum to form an oil;*

*(viii) distilling said oil under reduced pressure to provide an extracted intermediate;*

*(ix) reacting the extracted intermediate with semicarbazide; and*

*(x) collecting the resulting precipitate of the desired compound.*

*45. The method of claim 44, wherein at (i) said solvent is dimethylacetamide.*

*46. The method of claim 44, wherein at (i) said temperature is about 155° C.*

*47. The method of claim 44, wherein at (i) the molar ratio of said corresponding (thio)phenol and said fluorobenzaldehyde or fluoroaryl ketone is 0.15:0.14.*

*48. The method of claim 44, wherein at (v) said dilute aqueous sodium hydroxide is about 4% sodium hydroxide and about 96% water (weight/volume).*

* * * * *